US012105482B2

(12) United States Patent
Fukui et al.

(10) Patent No.: US 12,105,482 B2
(45) Date of Patent: Oct. 1, 2024

(54) ENVIRONMENT CONTROL SYSTEM

(71) Applicant: DAIKIN INDUSTRIES, LTD., Osaka (JP)

(72) Inventors: Sakiko Fukui, Osaka (JP); Miyae Yamakawa, Osaka (JP); Momoe Utsumi, Osaka (JP); Akari Higuchi, Osaka (JP); Haruka Tanaka, Osaka (JP); Mamoru Okumoto, Osaka (JP); Masanobu Kawazoe, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/310,670

(22) PCT Filed: Mar. 12, 2020

(86) PCT No.: PCT/JP2020/010945
§ 371 (c)(1),
(2) Date: Aug. 17, 2021

(87) PCT Pub. No.: WO2020/189529
PCT Pub. Date: Sep. 24, 2020

(65) Prior Publication Data
US 2022/0043404 A1 Feb. 10, 2022

(30) Foreign Application Priority Data

Mar. 15, 2019 (JP) ................................ 2019-049194
Jan. 10, 2020 (JP) ................................ 2020-003216

(51) Int. Cl.
*A61B 5/00* (2006.01)
*A61B 5/0205* (2006.01)
(Continued)

(52) U.S. Cl.
CPC ........ *G05B 13/0265* (2013.01); *A61B 5/0205* (2013.01); *A61B 5/02405* (2013.01);
(Continued)

(58) Field of Classification Search
CPC ..... A61B 5/0205; A61B 5/02405; A61B 5/11; A61B 5/165; A61B 5/202; A61B 5/441;
(Continued)

(56) References Cited

U.S. PATENT DOCUMENTS 9,189,599 B2 * 11/2015 Adler ..................... G16H 50/30
2009/0131758 A1 5/2009 Heywood et al.
(Continued)

FOREIGN PATENT DOCUMENTS

JP 2005-226882 8/2005
JP 2006-087850 4/2006
(Continued)

OTHER PUBLICATIONS

International Search Report mailed on Jun. 16, 2020, issued to PCT/JP2020/010945.
(Continued)

*Primary Examiner* — Sana Sahand
(74) *Attorney, Agent, or Firm* — IPUSA, PLLC

(57) ABSTRACT

An environment control system that controls an environment of a subject is provided. The environment control system includes an actuator configured to control an environment of a subject, and a controller configured to control an operation of the actuator. The environment control system includes an inference unit that includes a first learned model and a second learned model. The first learned model has been trained by associating environmental information indicating an environment of a subject with data correlating with one of sleep, excretion, movement, skin, and stress conditions of the subject. The second learned model has been trained by
(Continued)

associating the data correlating with one of the sleep, excretion, movement, skin, and stress conditions of the subject with data correlating with a magnitude of one or more risks that may occur with respect to the subject in a future period of time. The environment control system includes an operating condition determining unit configured to, in a case in which data correlating with the magnitude of the one or more risks that may occur with respect to a subject in a future period of time is inferred based on the first and second learned model, evaluate the inferred data to determine an operating condition of the actuator.

11 Claims, 22 Drawing Sheets

(51) Int. Cl.
*A61B 5/024* (2006.01)
*A61B 5/11* (2006.01)
*A61B 5/16* (2006.01)
*A61B 5/20* (2006.01)
*F24F 11/63* (2018.01)
*G05B 13/02* (2006.01)
*G16H 10/60* (2018.01)
*G16H 40/20* (2018.01)
*G16H 50/20* (2018.01)
*G16H 50/30* (2018.01)
*G16H 50/70* (2018.01)
*G06V 40/20* (2022.01)
*G16H 40/67* (2018.01)
*H04N 5/33* (2023.01)

(52) U.S. Cl.
CPC .............. *A61B 5/11* (2013.01); *A61B 5/165* (2013.01); *A61B 5/202* (2013.01); *A61B 5/441* (2013.01); *A61B 5/4812* (2013.01); *A61B 5/7267* (2013.01); *F24F 11/63* (2018.01); *G16H 10/60* (2018.01); *G16H 40/20* (2018.01); *G16H 50/20* (2018.01); *G16H 50/30* (2018.01); *G16H 50/70* (2018.01); *A61B 2560/0252* (2013.01); *A61B 2560/0257* (2013.01); *A61B 2562/029* (2013.01); *G06V 40/20* (2022.01); *G16H 40/67* (2018.01); *H04N 5/33* (2013.01)

(58) Field of Classification Search
CPC .............. A61B 5/4812; A61B 5/7267; G05B 13/0265; G16H 50/20; G16H 50/30; G16H 50/70; G16H 10/60; G16H 40/20
See application file for complete search history.

(56) References Cited

U.S. PATENT DOCUMENTS

| | | | |
|---|---|---|---|
| 2013/0246088 A1* | 9/2013 | Huster | G06Q 10/0635 705/2 |
| 2016/0078183 A1* | 3/2016 | Trygstad | G16H 50/20 706/11 |
| 2016/0350489 A1* | 12/2016 | Ribble | G16H 40/20 |
| 2017/0065827 A1* | 3/2017 | Fujiwara | A61N 5/0618 |
| 2018/0318602 A1* | 11/2018 | Ciccarelli | H05B 47/17 |
| 2020/0205727 A1* | 7/2020 | Shen | A61M 21/02 |
| 2020/0205741 A1* | 7/2020 | Laszlo | A61B 5/165 |

FOREIGN PATENT DOCUMENTS

| | | |
|---|---|---|
| JP | 2019-017499 | 2/2019 |
| WO | 2018/032089 | 2/2018 |

OTHER PUBLICATIONS

International Preliminary Report on Patentability for PCT/JP2020/010945 mailed on Sep. 30, 2021.

Extended European Search Report mailed on Nov. 4, 2022 with respect to the corresponding European patent application No. 20774021.8.

* cited by examiner

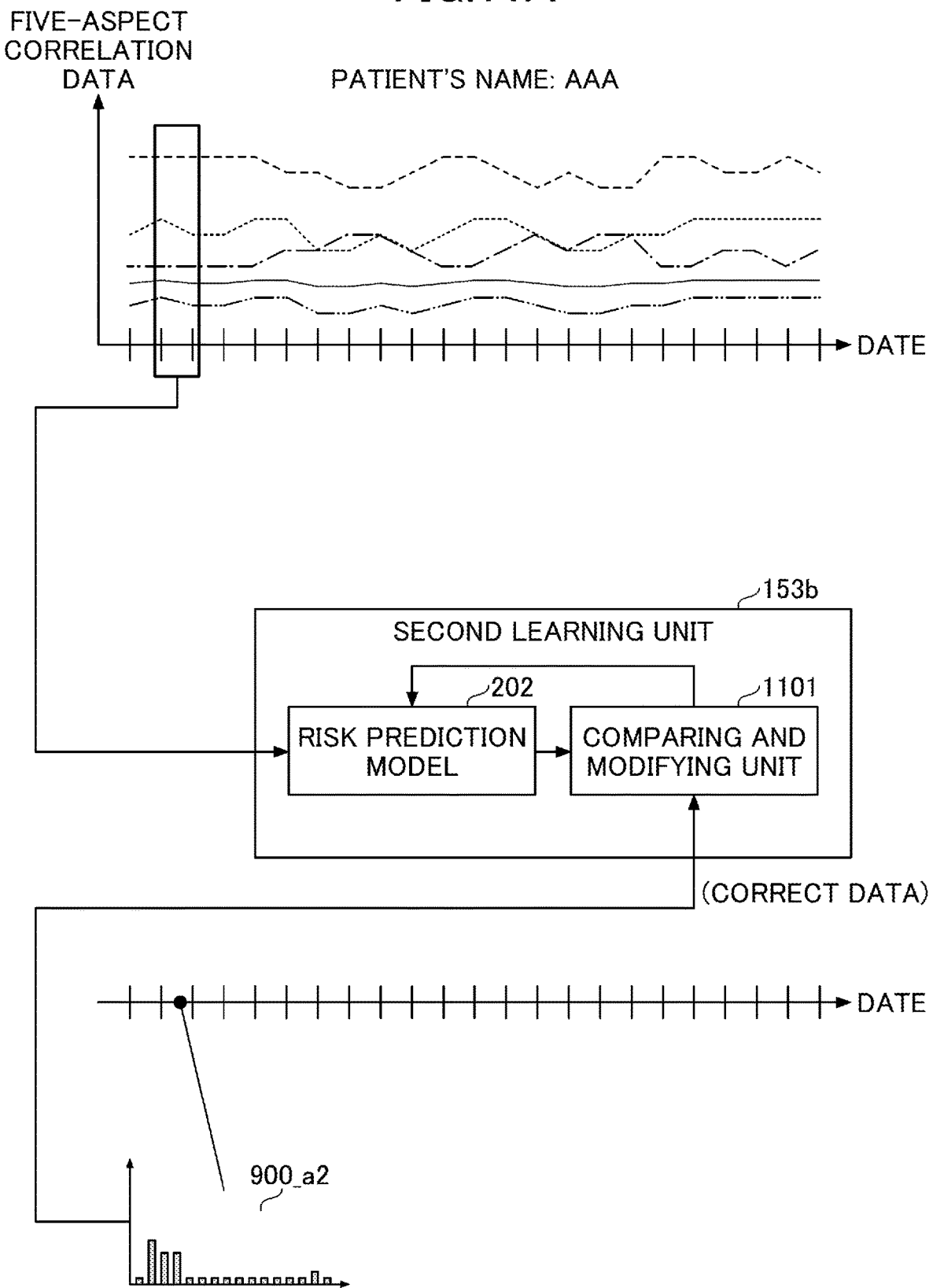

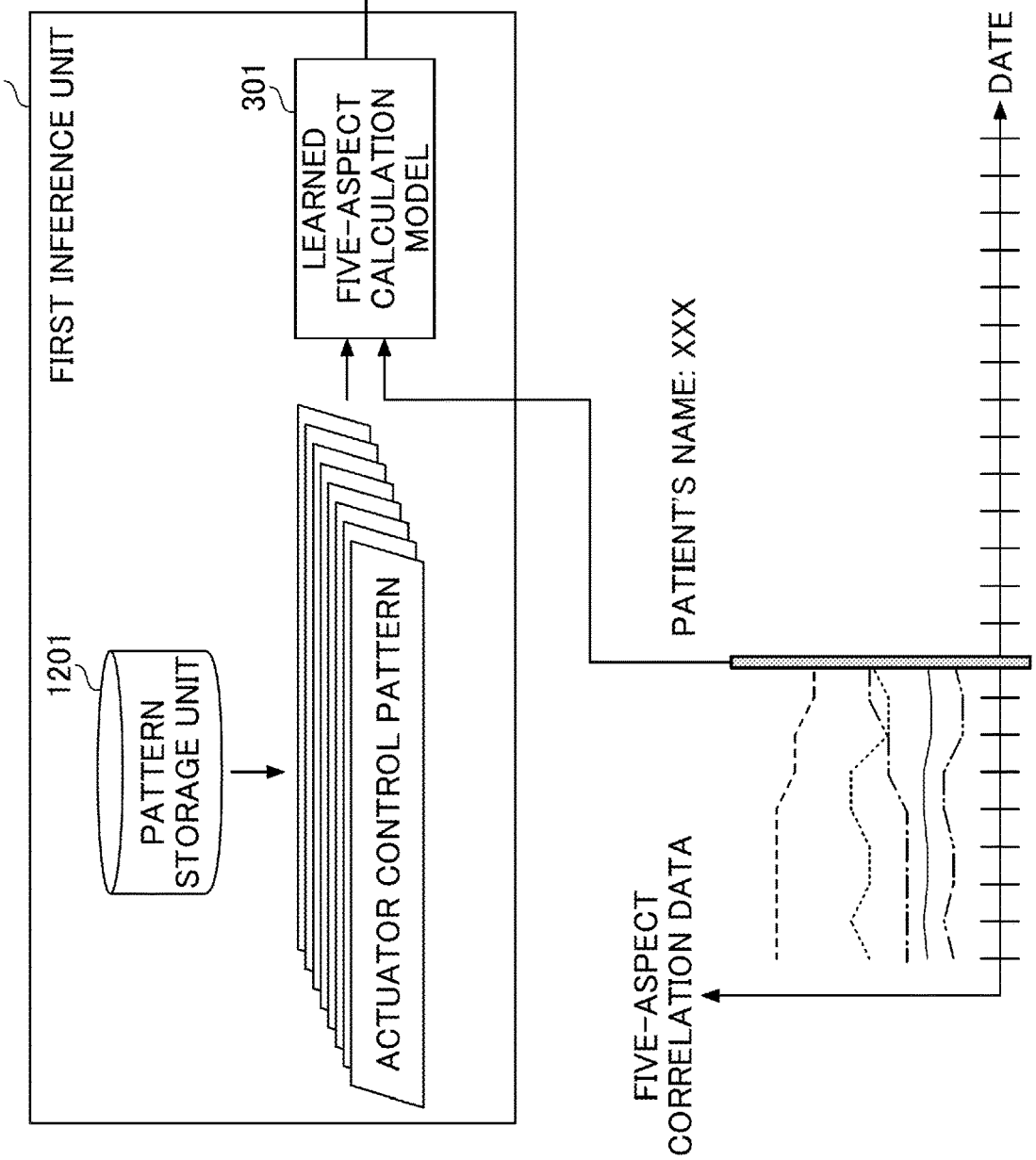

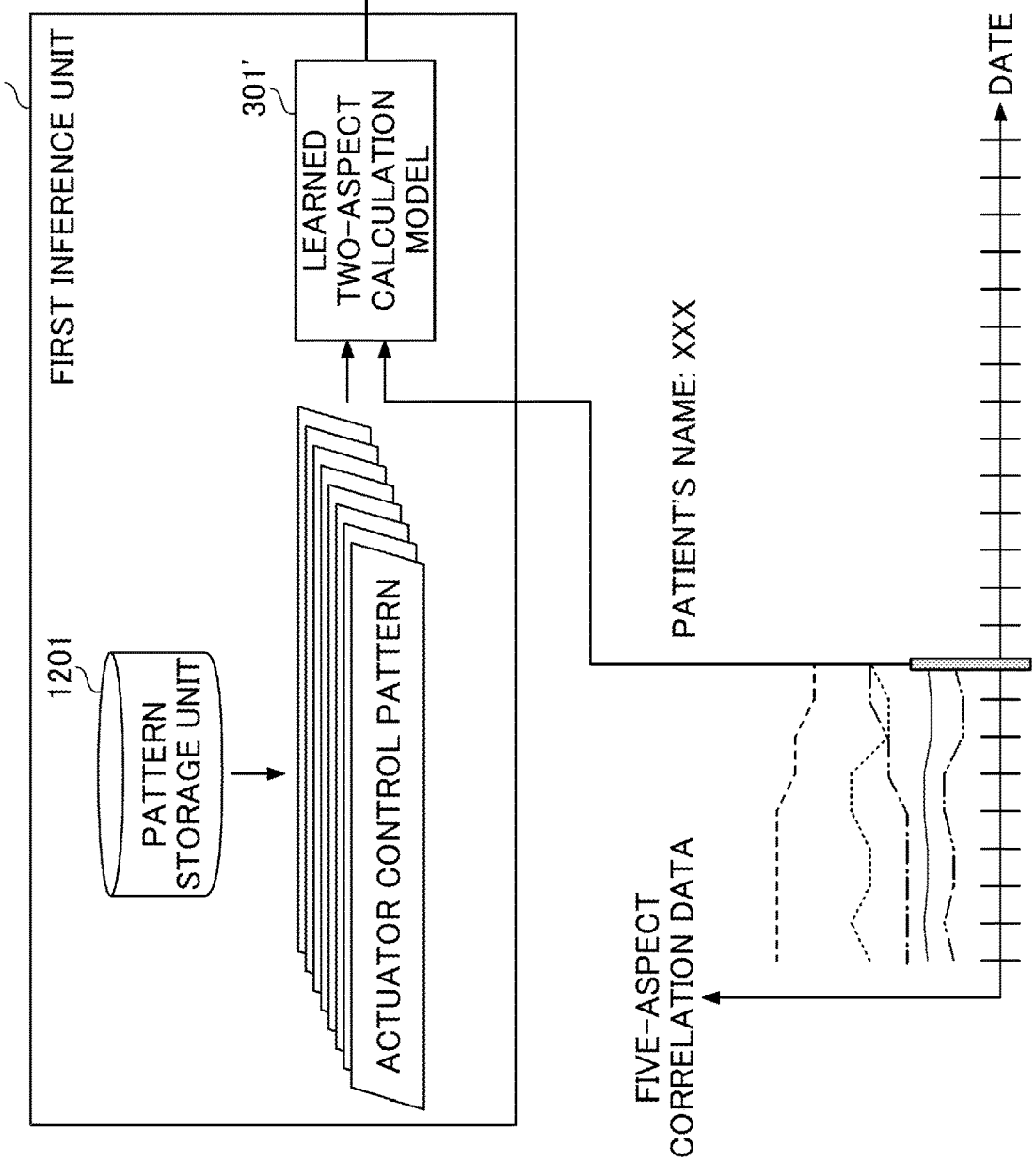

ENVIRONMENT CONTROL SYSTEM

TECHNICAL FIELD

The present disclosure relates to an environment control system.

BACKGROUND ART

Conventionally, various data related to patients has been obtained at a medical and caregiving site, such as sensing and recording biological information about patients in real time and recording daily conditions of patients as nursing records. By using such data, problems that have occurred in the patient can be accurately identified and medical care corresponding to the problems can be taken.

RELATED ART DOCUMENT

[Patent Document]
[Patent Document 1] Japanese Laid-open Patent Publication No. 2019-17499

SUMMARY OF THE INVENTION

Problem to be Solved by the Present Disclosure

If the risk of occurrence can be predicted before a problem occurs in the patient and an environment for the predicted risk can be provided to the patient, it is conceivable that the occurrence of the problem can be prevented and a contribution to the improvement of the quality of life (QOL) of the patient can be achieved.

The present disclosure provides an environment control system that controls an environment of a subject.

Means for Solving Problem

A first aspect of the present disclosure is an environment control system for controlling an environment of a subject and the environment control system includes an actuator configured to control an environment, an operating condition determining unit configured to determine an operating condition of the actuator, a controller configured to control the actuator based on the operating condition determined by the operating condition determining unit, and an inference unit that includes a first learned model and a second learned model. The first learned model is a model that has been trained by associating environmental information indicating an environment of a subject with data correlating with at least one of sleep, excretion, movement, skin, and stress conditions of the subject. The second learned model is a model that has been trained by associating the data correlating with the at least one of the sleep, excretion, movement, skin, and stress conditions of the subject with data correlating with a magnitude of one or more risks that may occur with respect to the subject in a future period of time. The inference unit infers data correlating with the magnitude of the one or more risks by inputting, into the second learned model, data that is output from the first learned model upon inputting environmental information about a subject into the first learned model, or a combination of the data output from the first learned model upon inputting the environmental information about the subject into the first learned model and data related to a condition of the subject. The operating condition determining unit evaluates the data correlating with the magnitude of the one or more risks that is inferred by the inference unit to determine the operating condition of the actuator.

According to the first aspect of the present disclosure, the environment control system that controls an environment of a subject can be provided.

A second aspect of the present disclosure is the environment control system described in the first aspect, wherein the second learned model is a model that has been trained by using biological information about the subject as the data correlating with the at least one of the sleep, excretion, movement, skin, and stress conditions of the subject.

A third aspect of the present disclosure is the environment control system described in the second aspect, wherein the biological information includes at least one of a movement distance of the subject, the number of times scratching of the subject, a fluctuation of the heart rate of the subject, a depth of sleep of the subject, an estimated amount of urine, and the number of excretions of the subject.

A fourth aspect of the present disclosure is the environment control system described in any one of the first to third aspects, wherein the first learned model is a model that has been trained by using the environmental information about the subject and the data correlating with the at least one of the sleep, excretion, movement, skin, and stress conditions of the subject as a training data set.

A fifth aspect of the present disclosure is the environment control system described in the fourth aspect, wherein the first learned model is a model that has further learned the data correlating with the at least one of the sleep, excretion, movement, skin, and stress conditions of the subject in association with a combination of the environmental information about the subject and attribute information indicating an attribute of the subject.

A sixth aspect of the present disclosure is the environment control system described in any one of the first to the fifth aspects, wherein the second learned model is a model that has been trained by using the data correlating with the sleep, excretion, movement, skin, and stress conditions of the subject and data correlating with the magnitude of one or more risks that may occur with respect to the subject in a future period of time as a training data set.

A seventh aspect of the present disclosure is the environment control system described in any one of the first to sixth aspects, wherein the inference unit uses a nursing record as the data related to the condition of the subject.

An eighth aspect of the present disclosure is the environment control system described in the first aspect, wherein the operating condition determining unit evaluates the data correlating with the magnitude of the one or more risks that is inferred by the inference unit by weighting and adding the data correlating with the magnitude of one or more risks.

A ninth aspect of the present disclosure is the environment control system described in the first aspect, wherein the environmental information includes at least one of the temperature, the humidity, the atmospheric pressure, the illuminance, and the noise.

A tenth aspect of the present disclosure is the environment control system described in the first aspect, wherein the actuator includes an air conditioning device that controls the environment of the subject.

An eleventh aspect of the present disclosure is an environment control system for controlling an environment of a subject, and the environment control system includes an actuator configured to control an environment, an operating condition determining unit configured to determine an operating condition of the actuator, a controller configured to control the actuator based on the operating condition determined by the operating condition determining unit, and an inference unit that includes a third learned model. The third learned model is a model that has been trained by associating data correlating with at least one of sleep, excretion, movement, skin, and stress conditions of a subject, and environmental information indicating the environment of the subject with data correlating with the magnitude of one or more risks that may occur with respect to the subject in a future period of time. The inference unit estimates data correlating with the magnitude of the one or more risks by inputting data correlating with at least one of sleep, excretion, movement, skin, and stress conditions of a subject and environmental information about the subject into the third learned model. The operating condition determining unit determines the operating condition of the actuator by evaluating the data correlating with the magnitude of the one or more risks that is inferred by the inference unit.

According to the eleventh aspect of the disclosure, the environment control system that controls the environment of the subject can be provided.

BRIEF DESCRIPTION OF THE DRAWINGS

FIG. 11A is a first diagram illustrating an example of a functional configuration of a second learning unit;

FIG. 12A is a first diagram illustrating an example of a functional configuration of a first inference unit;

FIG. 12B is a second diagram illustrating an example of the functional configuration of the first inference unit;

EMBODIMENT FOR CARRYING OUT THE INVENTION

Figure 1:
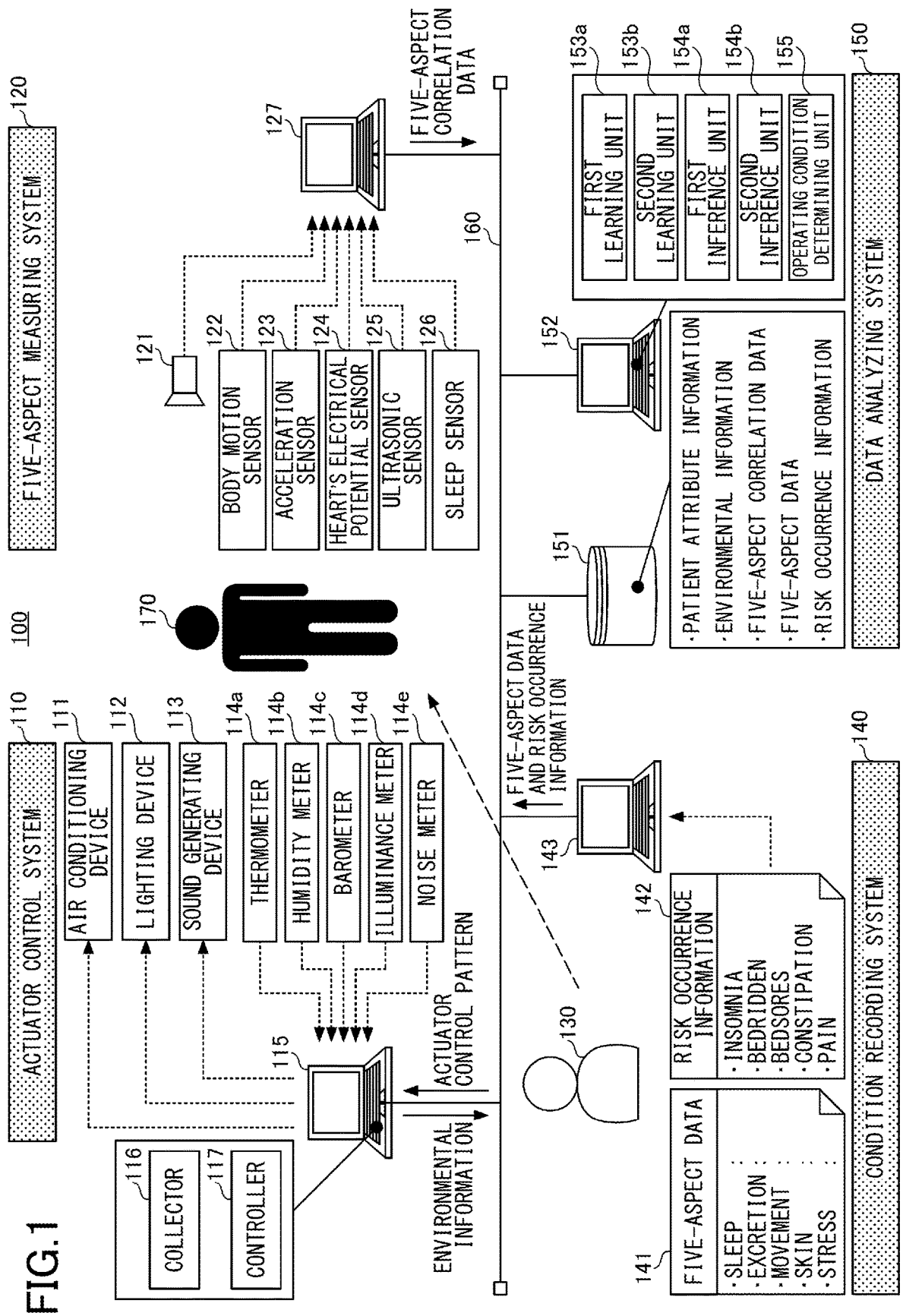
FIG. 1 is a diagram illustrating an example of a system configuration of an environment control system according to a first embodiment.

In the following, each embodiment will be described with reference to the accompanying drawings. In the present specification and the drawings, components having substantially the same functional configuration are referenced by the same reference numerals and duplicated description is omitted.

First Embodiment

<System Configuration of an Environment Control System>

First, a system configuration of an environment control system according to a first embodiment will be described. FIG. 1 is a diagram illustrating an example of the system configuration of the environment control system according to the first embodiment. The environment control system is installed in a hospital or a nursing home (in a case of home medical care, a private home of a patient that is an example of a subject). As illustrated in FIG. 1, the environment control system 100 includes an actuator control system 110, a five-aspect measuring system 120, a condition recording system 140, and a data analyzing system 150. In the environment control system 100, each system is connected through a network 160. A configuration of each system will be described below.

(1) Configuration of the Actuator Control System

The actuator control system 110 is a system that obtains environmental information indicating an environment of a patient by sensing an environment in a room where a patient 170 resides by using a sensing device, and controls the environment in the room where the patient 170 resides by using an actuator.

Specifically, the actuator control system 110 includes, as actuators, an air conditioning device 111, a lighting device 112, and a sound generating device 113. Additionally, the actuator control system 110 includes, as sensing devices, a thermometer 114a, a humidity meter 114b, a barometer 114c, an illuminance meter 114d, and a noise meter 114e. Further, the actuator control system 110 includes an actuator control device 115.

The air conditioning device 111 is a device that removes dirty substances of the air in the room where the patient 170 resides and controls the temperature and the humidity. The lighting device 112 is a device that controls the illuminance in the room where the patient 170 resides. The sound generating device 113 is a device that generates a sound, such as an audio device, a television, a radio, or the like, and controls the volume of the sound in the room where the patient 170 resides.

The air conditioning device 111, the lighting device 112, and the sound generating device 113 respectively control the temperature and humidity, the illuminance, and the volume of the sound, based on an instruction from the actuator control device 115.

The thermometer 114a and the humidity meter 114b sense the temperature and the humidity in the room where the patient 170 resides in a predetermined cycle, and transmit temperature data and humidity data to the actuator control device 115. The barometer 114c senses the atmospheric pressure in the room where the patient 170 resides in a predetermined cycle and transmits barometer data to the actuator control device 115.

The illuminance meter 114d senses the illuminance in the room where the patient 170 resides in a predetermined cycle and transmits illuminance data to the actuator control device 115. The noise meter 114e senses the sound in the room where the patient 170 resides in a predetermined cycle and transmits sound data to the actuator control device 115.

The actuator control device 115 includes a collector 116 and a controller 117. The collector 116 collects respective data sensed by the sensing devices and transmits the data to a data server 151 through the network 160 as the environmental information.

The controller 117 receives an actuator control pattern from the data analyzing system 150 through the network 160. Additionally, the controller 117 provides an instruction to control the temperature, the humidity, the illuminance, and the volume of the sound, to the air conditioning device 111, the lighting device 112, and the sound generating device 113 based on the received actuator control pattern. This allows the air conditioning device 111, the lighting device 112, and the sound generating device 113 to control the temperature, the humidity, the illuminance, and the volume of the sound based on the received actuator control pattern.

(2) Configuration of the Five-Aspect Measuring System

The five-aspect measuring system 120 is a system that senses data correlating with five aspects (sleep, excretion, movement, skin, and stress) of the patient 170 in biological information about the patient 170.

Specifically, the five-aspect measuring system 120 includes an infrared camera 121, a body motion sensor 122, an acceleration sensor 123, a heart's electrical potential sensor 124, an ultrasonic sensor 125, a sleep sensor 126, and a five-aspect measuring device 127.

The infrared camera 121 visualizes infrared rays emitted by the patient 170. By analyzing image data captured by the infrared camera 121, for example, the number of times scratching (the number of motions) in which the patient 170 scratches the skin at a particular site can be calculated. That is, the image data captured by the infrared camera 121 is data correlating with the "skin" among the five aspects of the patient 170. Additionally, by analyzing the image data captured by the infrared camera 121, for example, the amount of movement when the patient 170 leaves a bed and moves can be calculated. That is, the image data captured by the infrared camera 121 is also data correlating with the "movement" among the five aspects of the patient 170.

The body motion sensor 122 is a sensor that detects a body motion of the patient 170 on the bed, and for example, a Doppler sensor or the like is used. By analyzing body motion data detected by the body motion sensor 122, for example, the number of turns of the patient 170 in sleep can be calculated. That is, the body motion data detected by the body motion sensor 122 is data correlating with "sleep" among the five aspects of the patient 170. Additionally, based on the body motion data (i.e., vibration on the body surface) detected by the body motion sensor 122, for example, the fluctuation of the heart rate of the patient 170 can be calculated and the degree of stress (dominance of the sympathetic nerve or the parasympathetic nerve) of the patient 170 can be identified. That is, the body motion data detected by the body motion sensor 122 is also data correlating with "stress" among the five aspects of the patient 170.

The acceleration sensor 123 is a sensor that detects the movement of the patient 170. By analyzing acceleration data measured by the acceleration sensor 123, for example, the amount of movement of the patient 170 can be calculated. That is, the acceleration data measured by the acceleration sensor 123 is the data correlating with "movement" among the five aspects of the patient 170. Additionally, if the acceleration sensor 123 is mounted on the arm of the patient 170, for example, the number of times scratching (the number of motions) in which the patient 170 scratches the skin at a particular site can be detected. That is, the acceleration data measured by the acceleration sensor 123 is also data correlating with "skin" among five aspects of the patient 170.

The heart's electrical potential sensor 124 is a sensor that measures a heart's electrical potential of the patient 170. By analyzing the heart's electrical potential data measured by the heart's electrical potential sensor 124, for example, the fluctuation of the heart rate of the patient 170 can be calculated and the degree of stress (dominance of the sympathetic nerve or the parasympathetic nerve) of the patient 170 can be identified. That is, the heart's electrical potential data measured by the heart's electrical potential sensor 124 is data correlating with "stress" among the five aspects of the patient 170.

The ultrasonic sensor 125 is a sensor that measures the amount of urine stored in the bladder of the patient 170. By analyzing ultrasonic data measured by the ultrasonic sensor 125, for example, the estimated amount of urine of the patient 170 can be calculated. That is, the ultrasonic data measured by the ultrasonic sensor 125 is data correlating with "excretion" among the five aspects of the patient 170.

The sleep sensor 126 is a sensor that measures a sleep and waking state of the patient 170. By analyzing sleep data measured by the sleep sensor 126 in combination with, for example, the number of turns of the patient 170 in sleep, the sleep depth of the patient 170 can be calculated. That is, the sleep data measured by the sleep sensor 126 is data correlating with "sleep" among the five aspects of the patient 170.

The above-described sensing devices included in the five-aspect measuring system 120 are examples, and the five-aspect measuring system 120 may include a sensing device other than the above described sensing devices. For example, an electroencephalogram sensor, an RGB camera, a sound detection sensor, or the like may be disposed, and data detected by such a sensing device may be used as data correlating with "sleep", "movement", "skin", or the like.

The five-aspect measuring device 127 obtains the image data captured by the infrared camera 121, the body motion data detected by the body motion sensor 122, and the acceleration data measured by the acceleration sensor 123. Additionally, the five-aspect measuring device 127 obtains the heart's electrical potential data measured by the heart's electrical potential sensor 124, the ultrasonic data measured by the ultrasonic sensor 125, and the sleep data measured by the sleep sensor 126. Further, the five-aspect measuring device 127 calculates data correlating with the five aspects based on the obtained data and transmits the data to the data server 151 as the five-aspect correlation data through the network 160.

Here, the above description assumes the following.

As the data correlating with the "skin", the number of times scratching of the skin is calculated based on the image data.

As the data correlating with the "sleep", the sleep depth is calculated based on the number of turns in sleep calculated based on the body motion data and the sleep and waking state calculated based on the sleep data.

As the data correlating with the "movement", the amount of movement is calculated based on the acceleration data.

As the data correlating with the "stress", the fluctuation of the heart rate is calculated based on the heart's electrical potential data.

As the data correlating with the "excretion", the estimated amount of urine is calculated based on the ultrasound data.

However, the data correlating with the five aspects is not limited to these, and the data used in calculating the data correlating to the five aspects is not limited to these. For example, as the data correlating with the "excretion", the number of excretions may be calculated based on the body motion data.

(3) Configuration of the Condition Recording System

The condition recording system 140 is a system to which the five-aspect data (sleep, excretion, movement, skin, and stress) and risk occurrence information included in a daily nursing record recorded by a nurse 130 who provides medical nursing care to the patient 170 are input.

Specifically, the condition recording system 140 includes a condition recording device 143. The nurse 130 inputs five-aspect data 141 and risk occurrence information 142 included in the daily nursing record to the condition recording device 143.

As illustrated in FIG. 1, the five-aspect data 141 includes items of "sleep", "excretion", "movement", "skin", and "stress", and the nurse 130 records, for example, the degree of each item in five levels by observing the patient 170.

The risk occurrence information 142 lists items of problem events that may occur in the patient 170 (risks), and the nurse 130 records whether the problem event has occurred by observing the patient 170. In the example of FIG. 1, as the problem events that may occur in the patient 170 (risks), "insomnia", "bedridden", "bedsores", "constipation", "pain", and the like are listed. Here, the problem events that may occur in the patient 170 (risks) are not limited to these.

The condition recording device 143 transmits the five-aspect data 141 and the risk occurrence information 142 input by the nurse 130 to the data server 151 through the network 160.

(4) Configuration of the Data Analyzing System

The data analyzing system 150 is a system that determines an optimum environment for preventing the occurrence of problem events and contributing to the improvement of the QOL for a new patient (i.e., a new subject) based on knowledge obtained by analyzing the stored data of multiple patients including the patient 170.

Specifically, the data analyzing system 150 includes a data server 151 and a data analyzing device 152.

The data server 151 is a server that stores data (a training data set) about multiple patients including the patient 170. In the data server 151, patient attribute information with respect to multiple patients including the patient 170 is stored.

Additionally, the data server 151 stores the environmental information transmitted from the actuator control system 110, the five-aspect correlation data transmitted from the five-aspect measuring system 120, and the five-aspect data and the risk occurrence information 142 transmitted from the condition recording system 140.

A data analyzing program is installed in the data analyzing device 152. When the program is executed, the data analyzing device 152 functions as a first learning unit 153a, a second learning unit 153b, a first inference unit 154a, a second inference unit 154b, and an operating condition determining unit 155.

The first learning unit 153a learns the five-aspect correlation data in association with the environmental information. The second learning unit 153b learns the data correlating with the magnitude of the one or more risks calculated based on the risk occurrence information in association with the five-aspect correlation data (and the five-aspect data).

The first inference unit 154a sequentially receives multiple environmental information obtained after the current environment of the new patient is changed based on multiple different actuator control patterns to infer the five-aspect correlation data. Here, the actuator control patterns refer to various patterns that define operating conditions for operating the air conditioning device 111, the lighting device 112, and the sound generating device 113.

The second inference unit 154b receives the five-aspect correlation data (or a combination of the five-aspect correlation data and the five-aspect data) inferred by the first inference unit 154a to infer data correlating with the magnitude of the one or more risks of the new patient.

The operating condition determining unit 155 evaluates the data correlating with the magnitude of the one or more risks that is inferred by the second inference unit 154b. Consequently, the operating condition determining unit 155 determines the optimum actuator control pattern. Additionally, the operating condition determining unit 155 transmits the determined actuator control pattern to the actuator control device 115 through the network 160.

<Outline of a Process of the Environment Control System>

Next, an outline of a process of the environment control system 100 will be described.

Figure 2:
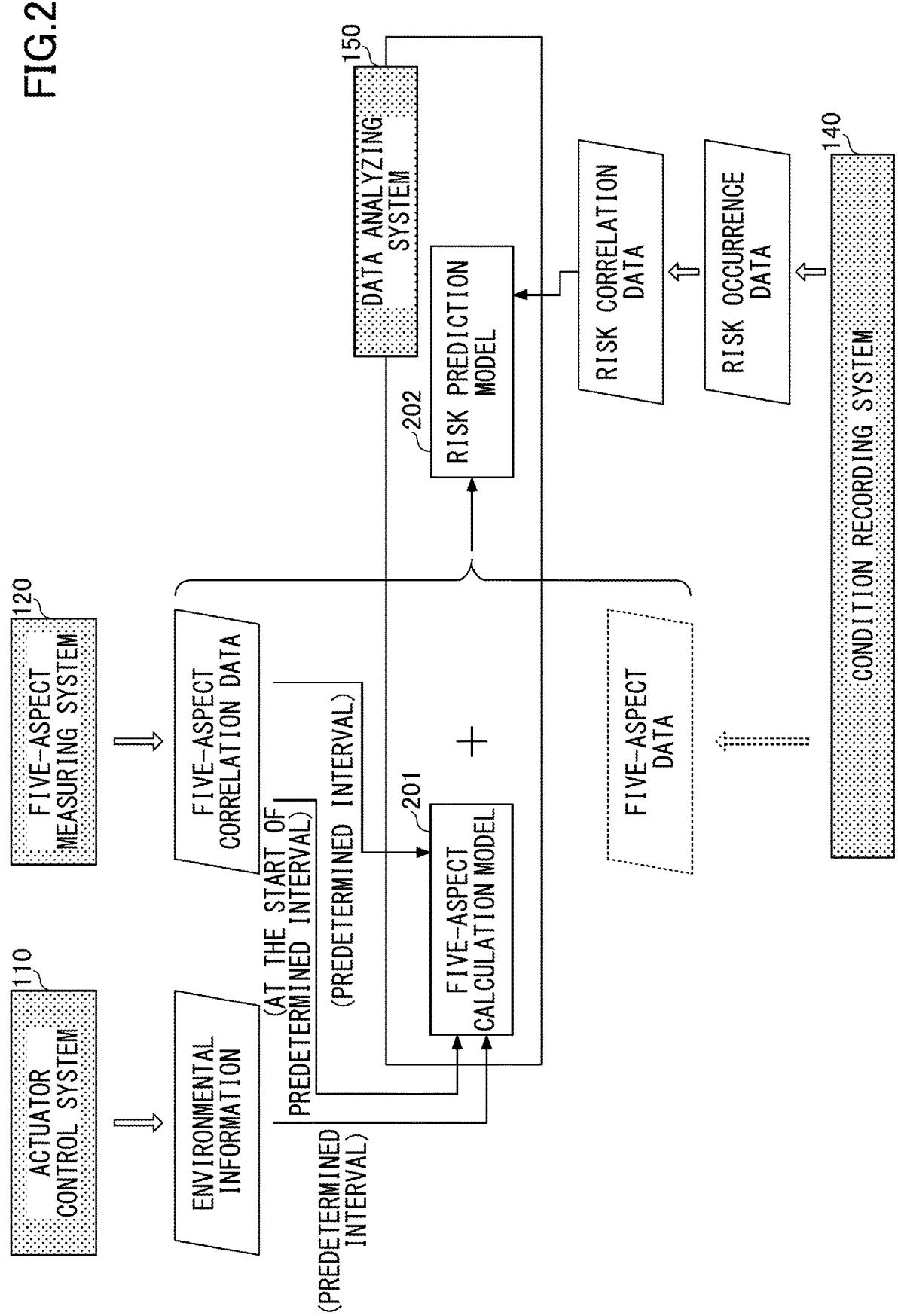
FIG. 2 is a diagram for explaining an outline of a process of the environment control system (a training phase) according to the first embodiment.

(1) Outline of a Process of the Environment Control System in the Training Phase First, an outline of a process of the environment control system 100 in the training phase will be described. FIG. 2 is a diagram for explaining an outline of the process of the environment control system (a training phase) according to the first embodiment.

As described above, in the data analyzing system 150, the first learning unit 153a learns the five-aspect correlation data in association with the environmental information. Specific process is as follows.

The environmental information for a predetermined interval (e.g., for one day) transmitted from the actuator control system 110 and the five-aspect correlation data, at the beginning of the predetermined interval, transmitted from the five-aspect measuring system 120 are input.

By using the five-aspect correlation data for the predetermined interval transmitted from the five-aspect measuring system 120 as correct data, machine learning is performed on a five-aspect calculation model 201, and a learned five-aspect calculation model is generated as a learned result.

Here, in the first learning unit 153a, the above-described machine learning is performed by using the training data set of the environmental information and the five-aspect correlation data of the multiple patients including the patient 170 stored in the data server 151.

As described above, in the data analyzing system 150, the second learning unit 153b learns data (risk correlation data) that correlates with the magnitude of risk calculated based on the risk occurrence information, in association with the five-aspect correlation data (and the five-aspect data). The specific process is as follows.

The five-aspect correlation data for a predetermined interval transmitted from the five-aspect measuring system 120 (and the five-aspect data transmitted from the condition recording system 140) is input.

By using the risk correlation data calculated based on the risk occurrence information transmitted from the condition recording system 140 as correct data, machine learning is performed on a risk prediction model 202 and a learned risk prediction model is generated as a learned result.

The second learning unit 153b performs the above-described machine learning by using the training data set of the five-aspect correlation data (and the five-aspect data) and the risk correlation data for the multiple patients including the patient 170 stored in the data server 151.

Figure 3:
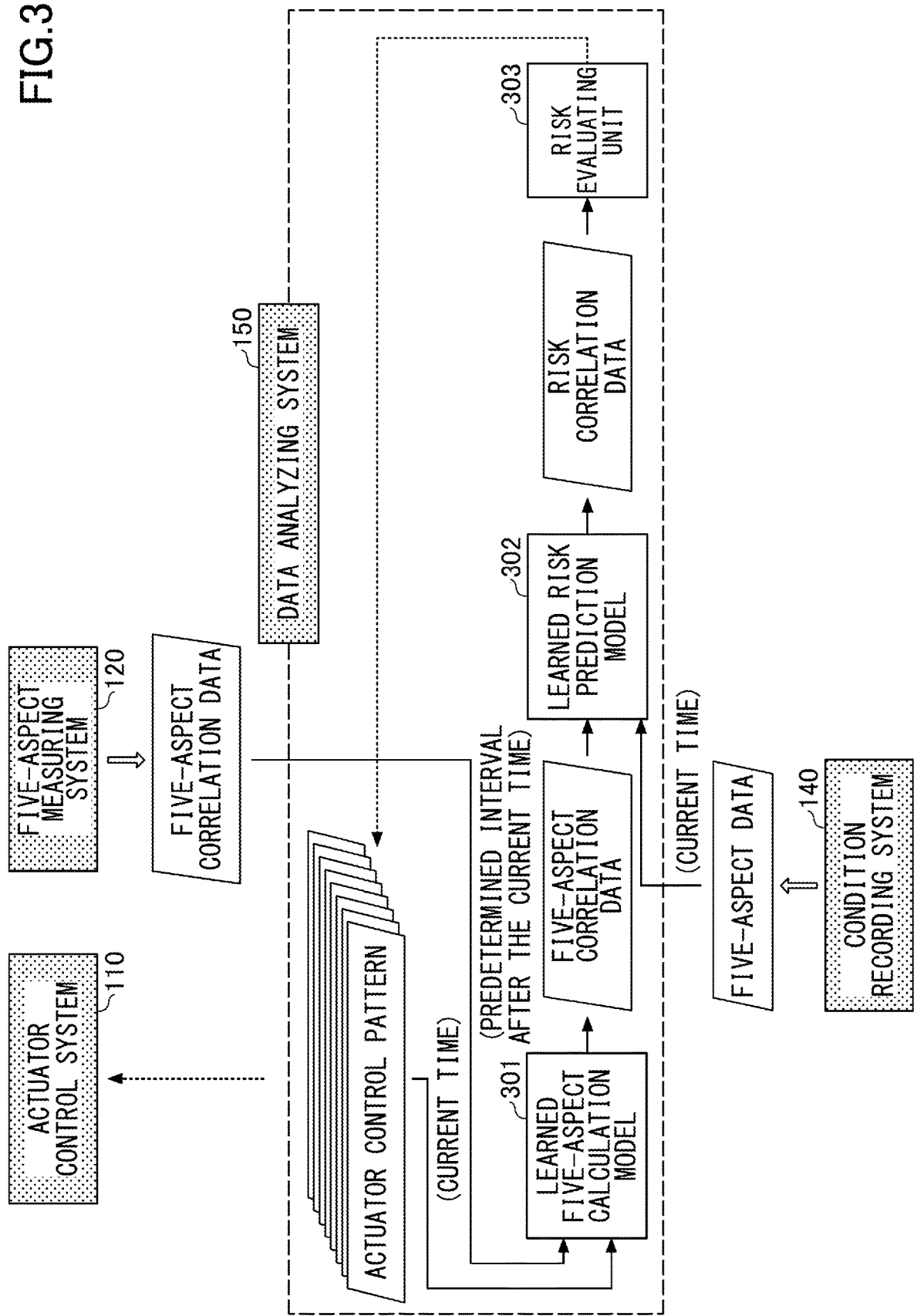
FIG. 3 is a diagram for explaining an outline of a process of the environment control system (an inference phase) according to the first embodiment.

(2) Outline of a Process of the Environment Control System in the Inference Phase Next, an outline of a process of the environment control system 100 in the inference phase will be described. FIG. 3 is a diagram for explaining the outline of the process of the environment control system (the inference phase) according to the first embodiment.

As described above, in the data analyzing system 150, the first inference unit 154a receives multiple environmental information obtained after the current environment of the new patient is changed based on multiple different actuator control patterns to infer the five-aspect correlation data.

Specifically, as illustrated in FIG. 3, in the data analyzing system 150, multiple actuator control patterns are retained in advance. Then, in the data analyzing system 150, a learned five-aspect calculation model 301, which is an example of a first learned model, is executed by inputting, one by one, environmental information obtained when the actuator is controlled by each of the actuator control patterns.

At this time, the data analyzing system 150 executes the learned five-aspect calculation model 301 by inputting the current five-aspect correlation data of the new patient transmitted from the five-aspect measuring system 120 together.

That is, the first inference unit 154a inputs a combination of the following data to infer five-aspect correlation data for a predetermined interval after the current time.

any one of the multiple actuator control patterns
the current five-aspect correlation data transmitted from the five-aspect measuring system 120

Additionally, in the data analyzing system 150, a learned risk prediction model 302, which is an example of a second learned model, is executed by inputting output data (the five-aspect correlation data) output from the learned five-aspect calculation model 301. Alternatively, in the data analyzing system 150, the learned risk prediction model 302 is executed by inputting a combination of the output data and the data related to the condition of the patient (the five-aspect data transmitted from the condition recording system 140).

Further, in the data analyzing system 150, a risk evaluating unit 303 evaluates the risk correlation data output from the learned risk prediction model 302. The risk evaluating unit 303 evaluates the risk correlation data output from the learned risk prediction model 302 every time one of the actuator control patterns is input to the learned five-aspect calculation model 301.

When the risk evaluating unit 303 completes the evaluation of all the risk correlation data, the actuator control pattern having the best evaluation result is identified. Then, the identified actuator control pattern is transmitted to the actuator control system 110 as the optimum actuator control pattern used to control the current environment of the new patient.

<Hardware Configuration of the Data Analyzing Device>

Figure 4:
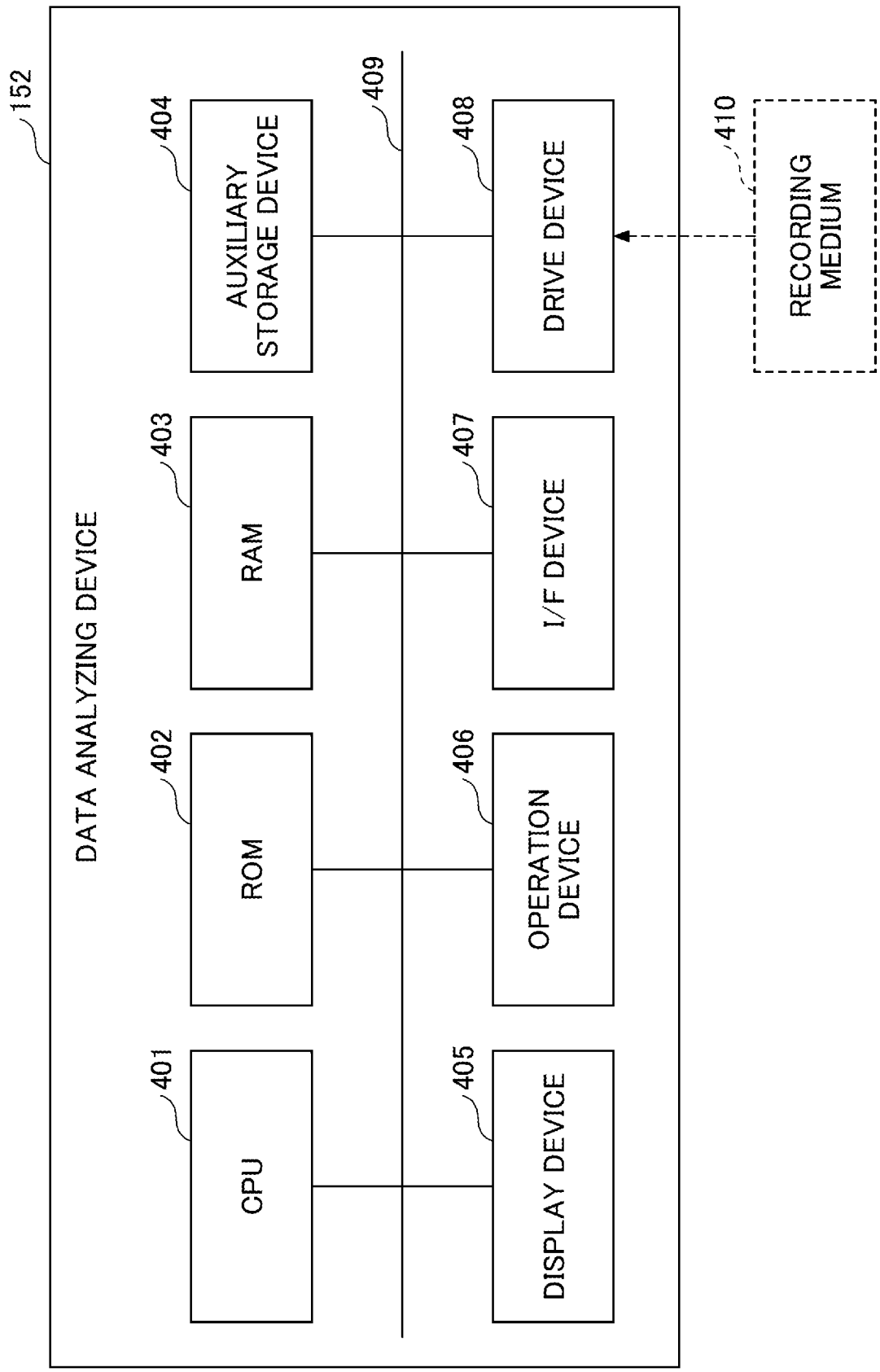
FIG. 4 is a diagram illustrating an example of a hardware configuration of a data analyzing device.

Next, a hardware configuration of the data analyzing device 152 will be described. FIG. 4 is a diagram illustrating an example of the hardware configuration of the data analyzing device. As illustrated in FIG. 4, the data analyzing device 152 includes a central processing unit (CPU) 401, a read only memory (ROM) 402, and a random access memory (RAM) 403. The CPU 401, the ROM 402, and the RAM 403 form what is called a computer. Additionally, the data analyzing device 152 includes an auxiliary storage device 404, a display device 405, an operation device 406, an interface (I/F) device 407, and a drive device 408. Each hardware component of the data analyzing device 152 is interconnected through a bus 409.

The CPU 401 is an arithmetic device that executes various programs (e.g., a data analysis program) installed in the auxiliary storage device 404. The ROM 402 is a non-volatile memory. The ROM 402 functions as a main storage device and stores various programs, data, and the like required for the CPU 401 to execute various programs installed in the auxiliary storage device 404. Specifically, the ROM 402 stores a boot program, such as a basic input/output system (BIOS) and an extensible firmware interface (EFI).

The RAM 403 is a volatile memory such as a dynamic random access memory (DRAM) or a static random access memory (SRAM). The RAM 403 functions as a main storage device and provides a workspace deployed when various programs installed in the auxiliary storage device 404 are executed by the CPU 401.

The auxiliary storage device 404 stores various programs and information used when various programs are executed.

The display device 405 is a display device that displays an internal state of the data analyzing device 152. The operation device 406 is, for example, an operation device used by an administrator of the data analyzing device 152 to perform various operations on the data analyzing device 152. The I/F device 407 is a connection device that connects to the network 160 to receive data.

The drive device 408 is a device that sets a recording medium 410. The recording medium 410 includes a medium that optically, electrically, or magnetically records information, such as a CD-ROM, a flexible disk, or a magneto-optical disk. Additionally, the recording medium 410 may include a semiconductor memory or the like that electrically records information, such as a ROM, or a flash memory.

Here, the various programs to be installed in the auxiliary storage device 404 are installed, for example, when the distributed recording medium 410 is set in the drive device 408 and the various programs recorded in the recording medium 410 are read by the drive device 408. Alternatively, the various programs to be installed in the auxiliary storage device 404 may be installed by a download from the network 160.

Although the hardware configuration of the data analyzing device 152 has been described in FIG. 4, the actuator control device 115, the five-aspect measuring device 127, and the condition recording device 143 may have the substantially same hardware configuration.

<Data Stored in the Data Server>

Next, a specific example of a training data set (the patient attribute information, the environmental information, the five-aspect correlation data, the five-aspect data, and the risk occurrence information) stored in the data server 151 will be described.

(1) Specific Example of the Patient Attribute Information

Figure 5:
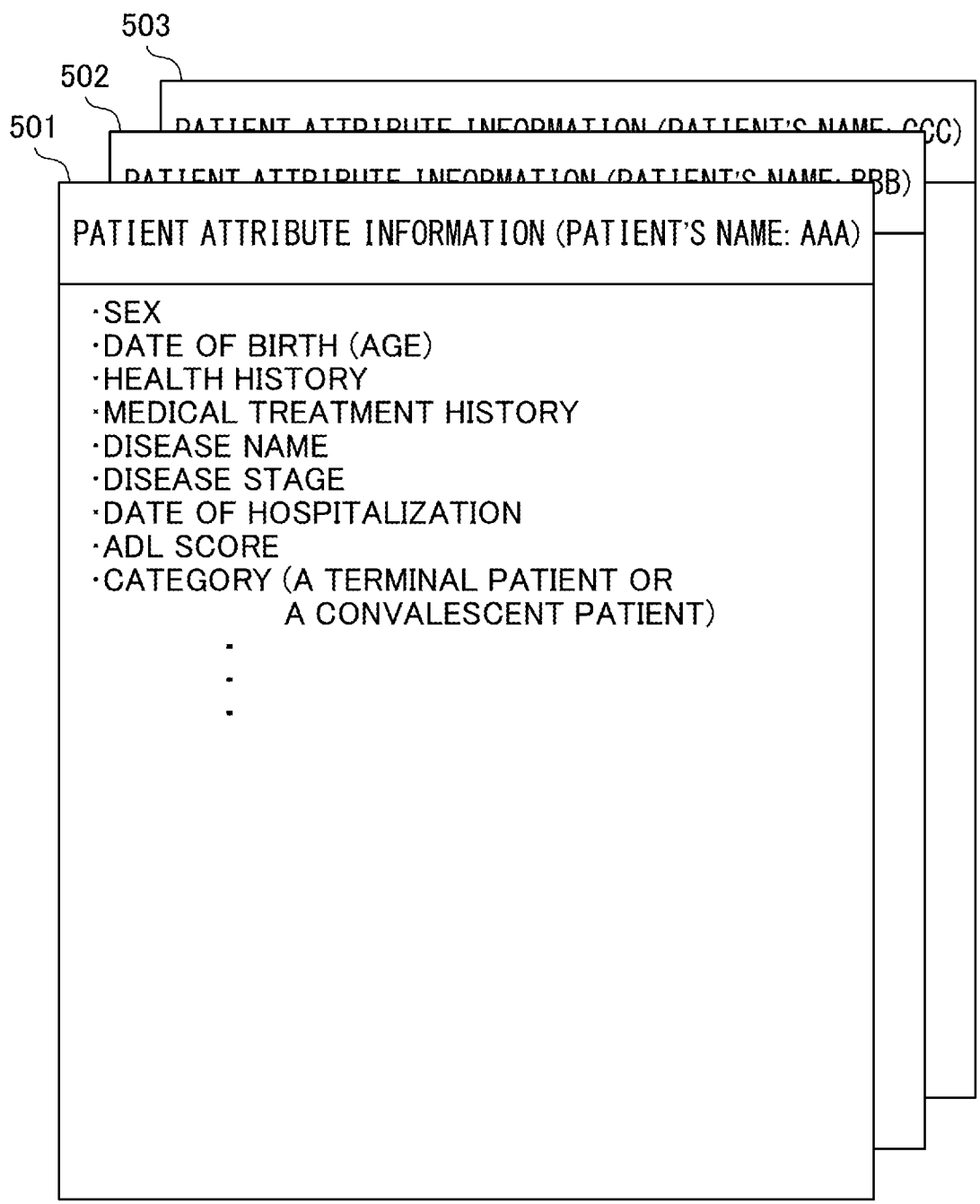
FIG. 5 is a diagram illustrating an example of attribute information about a patient.

First, a specific example of the patient attribute information will be described. FIG. 5 is a diagram illustrating an example of the patient attribute information. The patient attribute information is generated for each patient and stored in the data server 151. The example of FIG. 5 indicates patient attribute information 501 to 503 for respective patients having names="AAA", "BBB", and "CCC".

As illustrated in FIG. 5, the patient attribute information 501 to 503 includes items of information such as "sex", "date of birth (age)", "health history", "medical treatment history", "disease name", "disease stage", "date of hospitalization", "ADL score", "category (a terminal patient or a convalescent patient)", and the like.

(2) Specific Example of the Environmental Information

Figure 6:
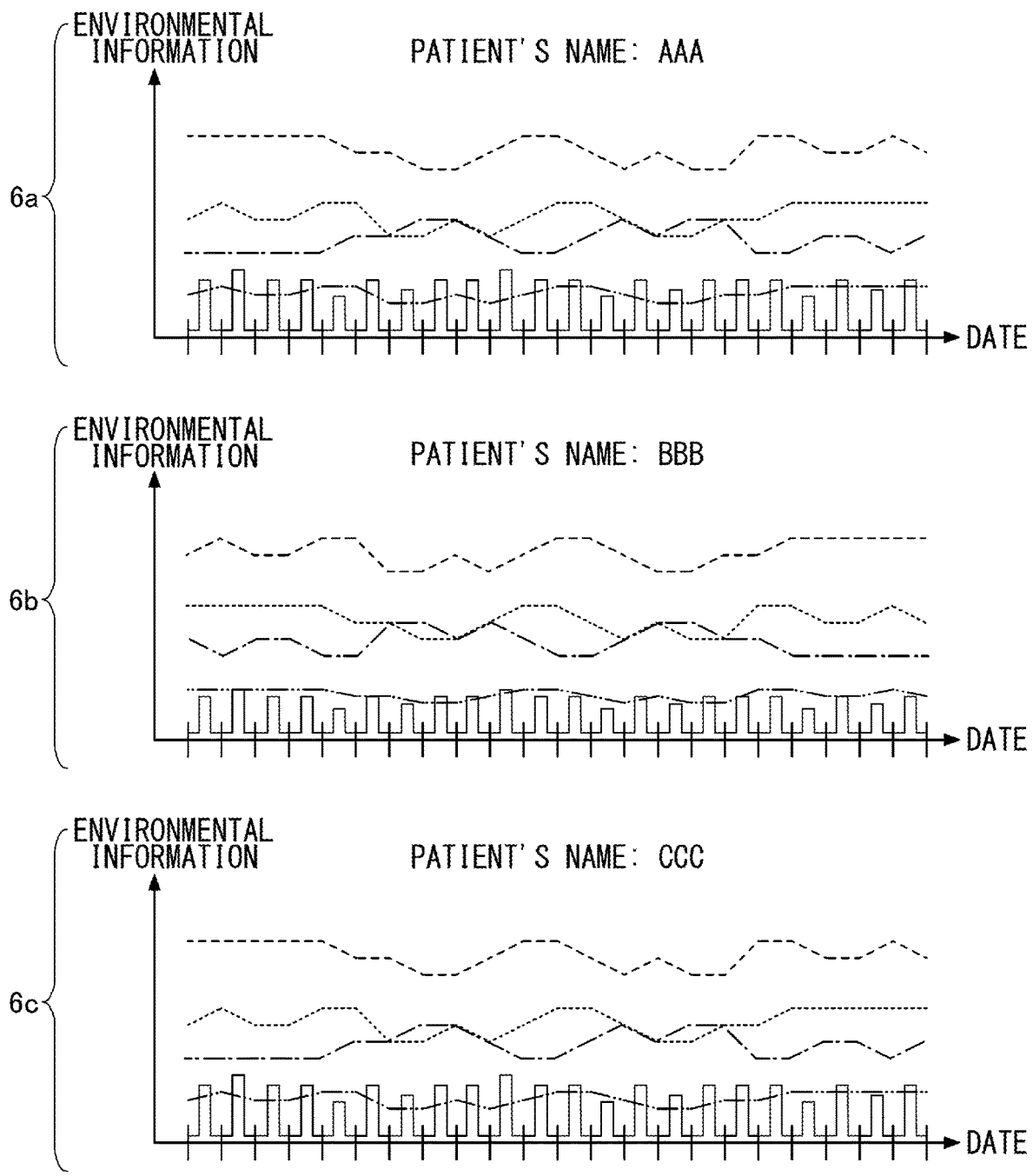
FIG. 6 is of graphs illustrating an example of environmental information.

Next, a specific example of the environmental information will be described. FIG. 6 is of graphs illustrating the example of the environmental information. The environmental information is obtained for each patient and stored in the data server 151 in association with the patient attribute information.

In the environmental information illustrated in FIG. 6, the horizontal axis represents the date and the vertical axis represents the environmental information. In the graphs, 6*a* of FIG. 6 illustrates data for a predetermined period of time with respect to the temperature, the humidity, the pressure, the illuminance, and the noise in the room where the patient whose name is "AAA" resides. Similarly, 6*b* of FIG. 6 illustrates data for a predetermined period of time with respect to the temperature, the humidity, the atmospheric pressure, the illuminance, and the noise in the room where the patient whose name is "BBB" resides. Similarly, FIG. 6*c* illustrates data for a predetermined period of time with respect to the temperature, the humidity, the atmospheric pressure, the illuminance, and the noise in the room where the patient whose name is "CCC" resides.

(3) Specific Example of the Five-Aspect Correlation Data

Figure 7:
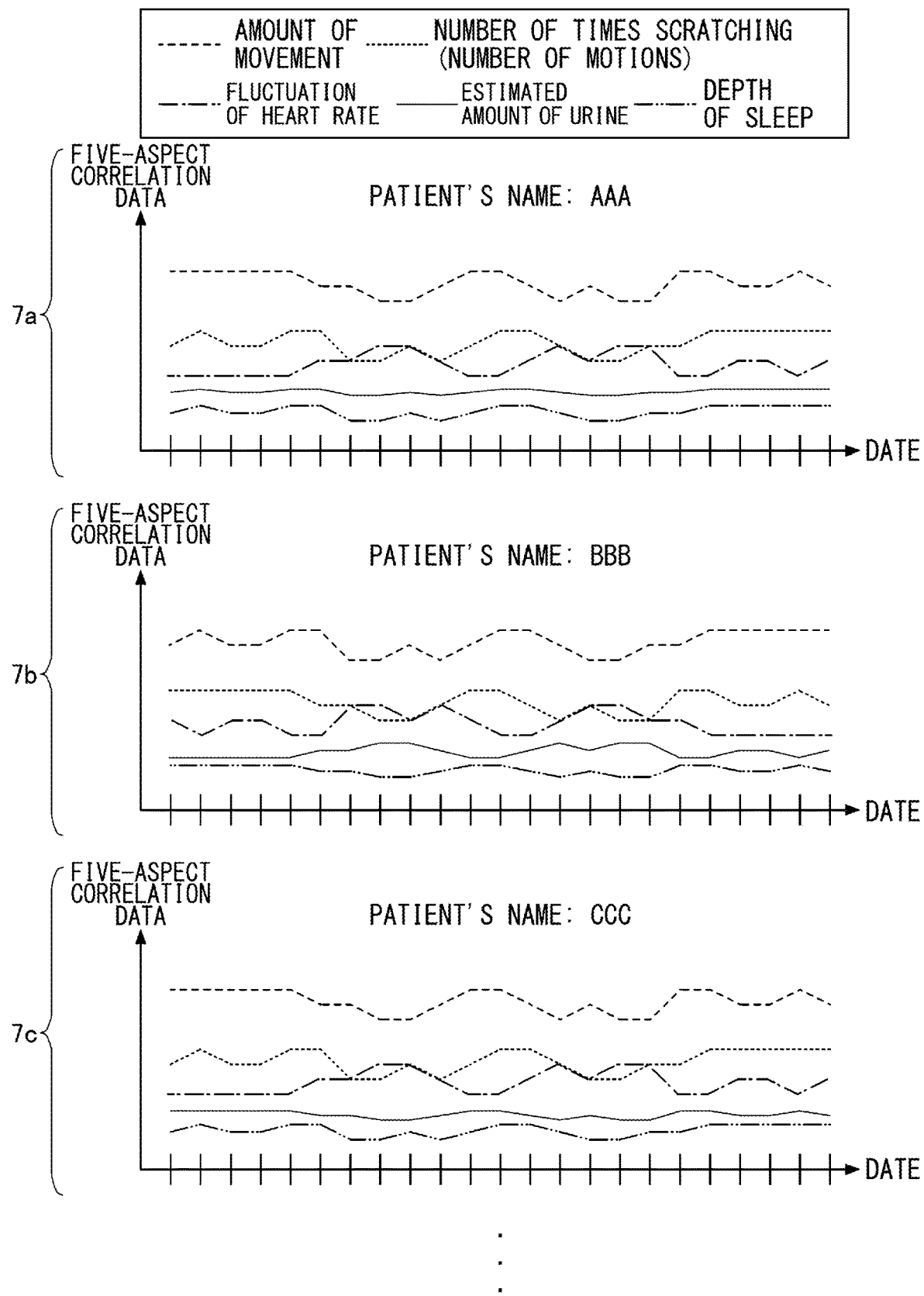
FIG. 7 is of graphs illustrating an example of five-aspect correlation data.

Next, a specific example of the five-aspect correlation data will be described. FIG. 7 is of graphs illustrating the example of the five-aspect correlation data. The five-aspect correlation data is obtained for each patient and stored in the data server 151 in association with the patient attribute information.

In the five-aspect correlation data illustrated in FIG. 7, the horizontal axis represents the date and the vertical axis represents the five-aspect correlation data. In the graphs, 7*a* of FIG. 7 indicates data for a predetermined period of time with respect to the amount of movement, the number of times scratching (the number of motions), the fluctuation of the heart rate, the estimated amount of urine, and the depth of sleep, of the patient whose name is "AAA".

Similarly, 7*b* of FIG. 7, indicates data for a predetermined period of time with respect to the amount of movement, the number of times scratching (the number of motions), the fluctuation of the heart rate, the estimated amount of urine, and the depth of sleep of the patient whose name is "BBB". Similarly, 7*c* of FIG. 7 indicates data for a predetermined period of time with respect to the amount of movement, the number of times scratching (the number of motions), the fluctuation of the heart rate, the estimated amount of urine, and the depth of sleep of the patient whose name is "CCC".

(4) Specific Example of the Five-Aspect Data

Figure 8:
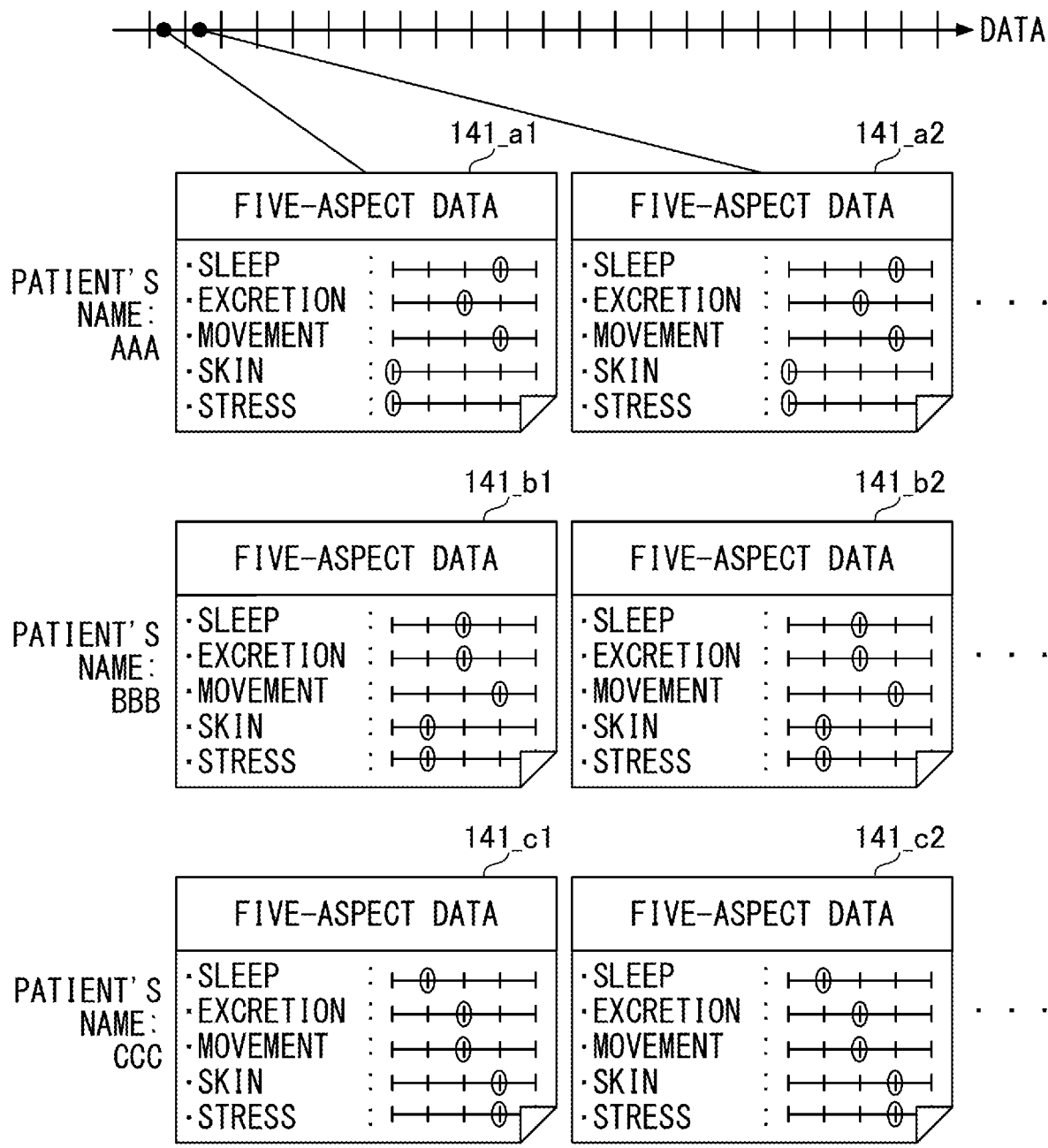
FIG. 8 is a diagram illustrating an example of five-aspect data.

Next, a specific example of the five-aspect data will be described. FIG. 8 is a diagram illustrating the example of the five-aspect data. The five-aspect data is obtained for each patient and stored in the data server 151 in association with the patient attribute information.

In the five-aspect data illustrated in FIG. 8, the horizontal axis represents the date. The five-aspect data referring to each date indicates five-aspect data recorded by the nurse 130 at that date. For example, five-aspect data 141_*a*1 represents the five-aspect data of the patient whose name is "AAA" on the first day of the predetermined period of time. Five-aspect data 141_*a*2 represents the five-aspect data of the patient whose name is "AAA" on the second day of the predetermined period of time.

In the following, similarly, five-aspect data 141_*b*1 and 141_*b*2 represent the five-aspect data of the patient whose name is BBB on the first day and the second day, and the five-aspect data 141_*c*1 and 141_*c*2 represent the five-aspect data of the patient whose name is CCC on the first day and the second day.

Here, as illustrated in FIG. 8, the five-aspect data records five levels of the respective degrees of "sleep", "excretion", "movement", "skin", and "stress".

(5) Specific Example of the Risk Occurrence Information

Figure 9:
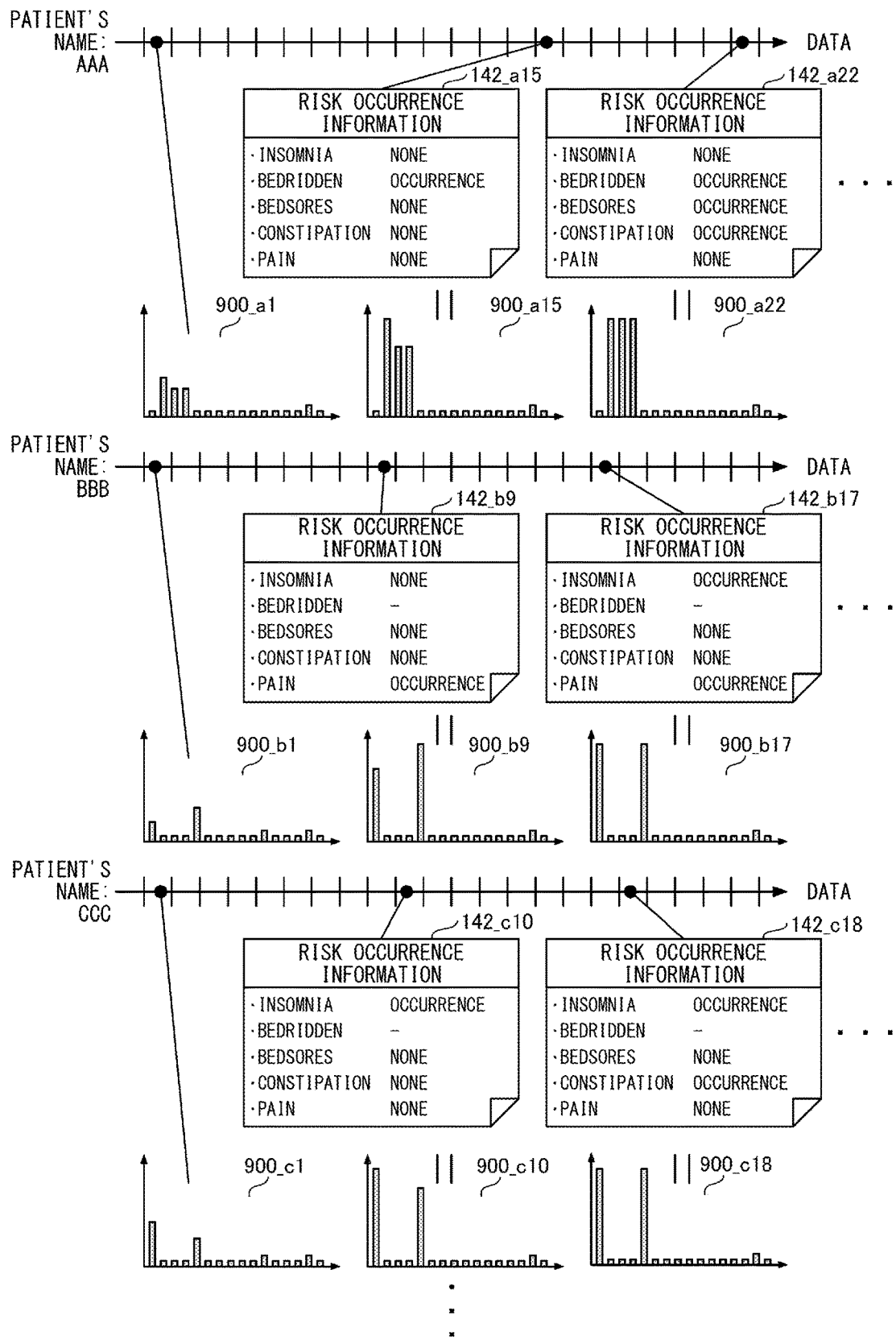
FIG. 9 is a diagram illustrating an example of risk occurrence information and risk correlation data.

Next, a specific example of the risk occurrence information and a specific example of the risk correlation data calculated based on the risk occurrence information will be described. FIG. 9 is a diagram illustrating an example of the risk occurrence information and the risk correlation data.

The risk occurrence information and the risk correlation data are obtained and calculated for each patient, and the risk occurrence information is stored in the data server 151 in association with the patient attribute information.

In the risk occurrence information and the risk correlation data illustrated in FIG. 9, the horizontal axis represents the date. The risk occurrence information referring to each date indicates the risk occurrence information recorded by the nurse 130 on that date. For example, risk occurrence information 142_*a*15 represents the risk occurrence information about the patient whose name is "AAA" on the 15th day of the predetermined period of time. Additionally, risk occurrence information 142_*a*22 represents the risk occurrence information about the patient whose name is "AAA" on the 22nd day of the predetermined period of time.

Graphs 900_*a*1, 900_*a*15, and 900_*a*22 respectively represent the risk correlation data of the patient whose name is "AAA" on the first day, the 15th day, and the 22nd day of the predetermined period of time.

For example, according to the risk occurrence information 142_*a*22, for the patient whose name is "AAA", "bedridden", "bedsores", and "constipation" occur on the 22nd day of the predetermined period of time. Therefore, in the graph 900_*a*22, the risk correlation data for these items is 100%. Similarly, according to the risk occurrence information 142_*a*15, for the patient whose name is "AAA", "bedridden" occurs on the 15th day of the predetermined period of time. Therefore, in the graph 900_*a*15, the risk correlation data for that item is 100%.

With respect to the above, according to the risk occurrence information 142_*a*15, for the patient whose name is "AAA", "bedsores" and "constipation" do not occur on the 15th day of the predetermined period of time. However, as described above, these items occur on the 22nd day of the predetermined period of time. Therefore, on the 15th day of the predetermined period of time, the risk correlation data is approximately 70% (=15/22×100), as illustrated in graph 900_*a*15.

Similarly, on the first day of the predetermined period of time, no risk occurs, but "bedridden", "bedsores", "constipation" occur on the 15th or 22nd day of the predetermined period of time, respectively. Thus, on the first day of the predetermined period of time, each of the risk correlation data is approximately 7% or 5%, as illustrated in graph 900_a1.

Similarly, for example, risk occurrence information 142_b9 represents the risk occurrence information for the patient whose name is "BBB" on the ninth day of the predetermined period of time. Additionally, risk occurrence information 142_b17 represents the risk occurrence information for the patient whose name is "BBB" on the 17th day of the predetermined period.

The graphs 900_b1, 900_b9, and 900_b17 respectively represent the risk correlation data of the patient whose name is "BBB" on the first day, the 9th day, and the 17th day of the predetermined period of time.

For example, according to the risk occurrence information 142_b17, for the patient whose name is "BBB", "insomnia" and "pain" occur on the 17th day of the predetermined period of time. Thus, in the graph 900_b17, the risk correlation data for that item is 100%. Similarly, according to the risk occurrence information 142_b9, for the patient whose name is "BBB", "pain" occurs on the 9th day of the predetermined period of time. Thus, in the graph 900_b9, the risk correlation data for that item is 100%.

With respect to the above, according to the risk occurrence information 142_b9, for the patient whose name is "BBB", "insomnia" does not occur on the 9th day of the predetermined period of time. However, as described above, that item occurs on the 17th day of the predetermined period of time. Therefore, on the 9th day of the predetermined period, the risk correlation data is approximately 50% (=9/17×100), as illustrated in the graph 900_b9.

Similarly, on the first day of the predetermined period, no risk occurs, but "insomnia" and "pain" respectively occur on the 17th day and 9th day of the predetermined period. Thus, on the first day of the predetermined period, each of the risk correlation data is approximately 5% or approximately 10%, as illustrated in the graph 900_b1.

Similarly, for example, risk occurrence information 142_c10 represents the risk occurrence information for the patient whose name is "CCC" on the 10th day of the predetermined period of time. Additionally, risk occurrence information 142c18 represents the risk occurrence information about the patient whose name is "CCC" on the 18th day of the predetermined period of time.

The graphs 900_c1, 900_c10, and 900_c18 respectively represent the risk correlation data of the patient whose name="CCC" on the first day, the 10th day, and 18th day of the predetermined period of time.

For example, according to the risk occurrence information 142_c18, for the patient whose name is "CCC", "insomnia" and "constipation" occur on the 18th day of the predetermined period of time. Thus, in the graph 900_c18, the risk correlation data for those items is 100%. Similarly, according to the risk occurrence information 142_c10, for the patient whose name is "CCC", "insomnia" has occurred on the 10th day of the predetermined period of time. Thus, in the graph 900_c10, the risk correlation data for that item is 100%.

With respect to the above, according to the risk occurrence information 142_c10, for the patient whose name is "CCC", "constipation" does not occur on the 10th day of the predetermined period. However, as described above, this item occurs on the 18th day of the predetermined period of time. Thus, on the 10th day of the predetermined period of time, the risk correlation data is approximately 50% (=10/18×100).

Similarly, on the first day of the predetermined period of time, no risk occurs, but "insomnia" and "constipation" respectively occur on the 10th day and 18th day of the predetermined period of time. Thus, on the first day of the predetermined period of time, each of the risk correlation data is approximately 10% or 5%, as illustrated in the graph 900_c1.

<Functional Configuration of the First Learning Unit>

Next, a functional configuration of the first learning unit 153a of the data analyzing device 152 will be described. Here, a case of being trained by using a different data set will be described.

(1) First Case

Figure 10A:
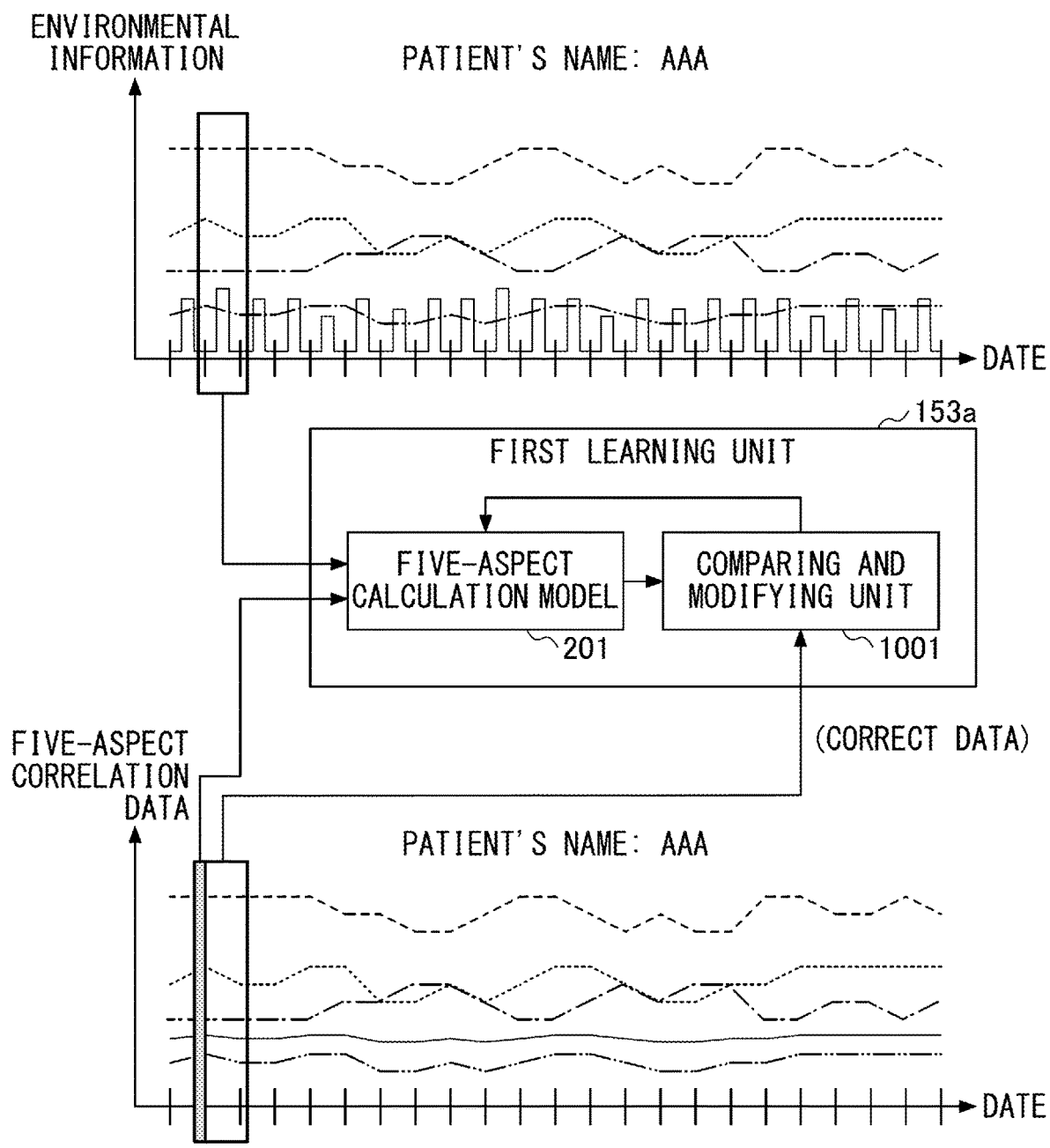
FIG. 10A is a first diagram illustrating an example of a functional configuration of a first learning unit.

FIG. 10A is a first diagram illustrating an example of a functional configuration of the first learning unit. As illustrated in FIG. 10A, the first learning unit 153a includes the five-aspect calculation model 201 and a comparing and modifying unit 1001.

The first learning unit 153a reads the environmental information (in the example of FIG. 10A, the environmental information about the patient whose name is "AAA" on the second day) from the data server 151. Further, the first learning unit 153a reads the five-aspect correlation data (in the example of FIG. 10A, the five-aspect correlation data of the patient whose name="AAA" at the beginning of the second day and the five-aspect correlation data on the second day.

The first learning unit 153a inputs the environmental information on the second day among these into the five-aspect calculation model 201. Specifically, the first learning unit 153a inputs the temperature, the humidity, the atmospheric pressure, the illuminance, and the noise of the room for one day into the five-aspect calculation model 201. Here, the temperature, the humidity, the atmospheric pressure, the illuminance, and the noise in the room for one day that are input into the five-aspect calculation model 201 may be a transition of data for one day, or data obtained by calculating data for one day (e.g., an average value, a maximum value or a minimum value, variation, or the like).

The first learning unit 153a inputs the five-aspect correlation data at the beginning of the second day into the five-aspect calculation model 201. Specifically, the first learning unit 153a inputs data correlating with sleep, excretion, movement, skin, and stress conditions at the beginning of the second day into the five-aspect calculation model 201.

Then, the first learning unit 153a executes the five-aspect calculation model 201 and the five-aspect calculation model 201 outputs the five-aspect correlation data. Specifically, the five-aspect calculation model 201 outputs data correlating with the sleep, excretion, movement, skin, and stress conditions.

The five-aspect correlation data that is output from the five-aspect calculation model 201 is input into the comparing and modifying unit 1001. The comparing and modifying unit 1001 compares the following data.

the five-aspect correlation data that is output from the five-aspect calculation model 201 the five-aspect correlation data read from the data server 151 (the correct data)

The comparing and modifying unit 1001 modifies model parameters of the five-aspect calculation model 201 in accordance with a comparison result.

As described, the first learning unit 153a performs machine learning on the five-aspect calculation model 201 that determines a correspondence relationship between the following data.

the environmental information, for the predetermined interval, indicating the environment of the patient, and the five-aspect correlation data at the beginning of the predetermined interval the five-aspect correlation data of the patient for the predetermined interval Consequently, the first learning unit 153a generates the learned five-aspect calculation model for inferring the five-aspect correlation data as a trained result.

The example of FIG. 10 indicates a case in which the first learning unit 153a inputs the temperature, the humidity, the atmospheric pressure, the illuminance, and the noise in the room into the five-aspect calculation model 201 as the environmental information. However, the first learning unit 153a may be configured to input only part of these information into the five-aspect calculation model 201.

(2) Second Case

In the first case described above, the case in which the five-aspect calculation model 201 outputs the data correlating with the sleep, excretion, movement, skin, and stress conditions has been described. However, the five-aspect calculation model 201 may be configured to output only part of these data.

Figure 10B:
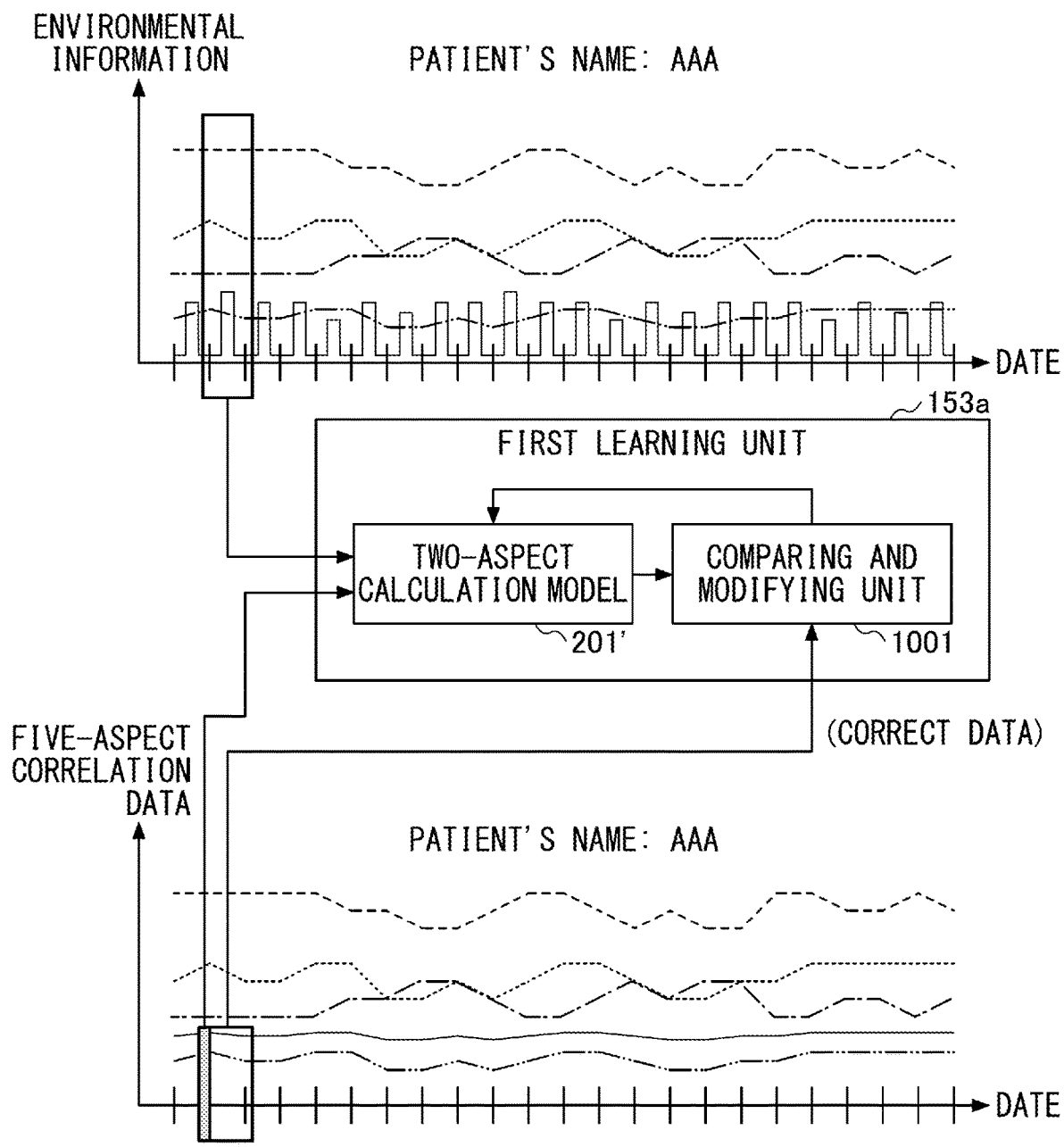
FIG. 10B is a second diagram illustrating an example of the functional configuration of the first learning unit.

FIG. 10B is a second diagram illustrating an example of a functional configuration of the first learning unit. A difference from FIG. 10A is that the first learning unit 153a reads two-aspect correlation data among the five-aspect correlation data. Specifically, data correlating the sleep and excretion conditions of the patient whose name is "AAA" at the beginning of the second day and data correlating the sleep and excretion conditions of the patient whose name is "AAA" on the second day are read.

In FIG. 10B, the first learning unit 153a inputs the environmental information on the second day and the two-aspect correlation data at the beginning of the second day into a two-aspect calculation model 201'. Then, the first learning unit 153a executes the two-aspect calculation model 201' and the two-aspect calculation model 201' outputs the two-aspect correlation data. Specifically, the two-aspect calculation model 201' outputs data correlating with sleep and excretion conditions.

The two-aspect correlation data that is output from the two-aspect calculation model 201' is input into the comparing and modifying unit 1001. The comparing and modifying unit 1001 compares the following data.

the two-aspect correlation data that is output from the two-aspect calculation model 201' the two-aspect correlation data read from the data server 151 (the correct data)

The comparing and modifying unit 1001 modifies model parameters of the two-aspect calculation model 201' in accordance with a comparison result.

As described above, the first learning unit 153a performs machine learning on the two-aspect calculation model 201' that determines a correspondence relationship between the following data.

the environmental information, for the predetermined interval, indicating the environment of the patient and the two-aspect correlation data at the beginning of the predetermined interval the two-aspect correlation data of the patient for the predetermined interval Consequently, the first learning unit 153a generates a learned two-aspect calculation model for inferring the two-aspect correlation data as a trained result.

In the example of FIG. 10B, the case in which the two-aspect correlation data is output has been described, but machine learning may be performed so that one-aspect correlation data, three-aspect correlation data, or four-aspect correlation data is output.

<Functional Configuration of the Second Learning Unit>

Next, a functional configuration of the second learning unit 153b of the data analyzing device 152 will be described. Again, a case in which training is performed by using a different data set will be described.

(1) First Case

FIG. 11A is a first diagram illustrating an example of the functional configuration of the second learning unit. As illustrated in FIG. 11A, the second learning unit 153b includes the risk prediction model 202 and a comparing and modifying unit 1101.

The second learning unit 153b reads the five-aspect correlation data (in the example of FIG. 11, the five-aspect correlation data of the patient whose name is "AAA" on the second day) from the data server 151. Additionally, the second learning unit 153b reads the risk occurrence information from the data server 151 and calculates the risk correlation data (in the example of FIG. 11, the risk correlation data of the patient whose name is "AAA" on the second day).

The second learning unit 153b inputs the five-aspect correlation data into the risk prediction model 202. Specifically, the second learning unit 153b inputs the data correlating with the sleep, excretion, movement, skin, and stress conditions into the risk prediction model 202.

Consequently, the second learning unit 153b executes the risk prediction model 202 and the risk prediction model 202 outputs the risk correlation data. Specifically, the risk prediction model 202 outputs the risk correlation data including items of "insomnia", "bedridden", "bedsores", "constipation", "pain", . . . , and the like.

The risk correlation data that is output from the risk prediction model 202 is input into the comparing and modifying unit 1101. The comparing and modifying unit 1101 compares the following data.

the risk correlation data output from the risk prediction model 202 the risk correlation data calculated based on the risk occurrence information that is read from the data server 151 (correct data)

The comparing and modifying unit 1101 modifies model parameters of the risk prediction model 202 in accordance with a comparison result.

As described, the second learning unit 153b performs machine learning on the risk prediction model 202 that determines a correspondence relationship between the following data.

the five-aspect correlation data of the patient for the predetermined interval the risk correlation data of the one or more future risks that may occur with respect to the patient for the predetermined interval Then, the second learning unit 153b generates a learned risk prediction model for inferring the risk correlation data.

(2) Second Case

In the first case described above, the case in which the second learning unit 153b inputs, as the five-aspect correlation data, the data correlating with the sleep, excretion, movement, skin, and stress conditions into the risk prediction model 202, has been described. However, the second learning unit 153b may input only part of these data into the risk prediction model 202 and additionally input part of the five-aspect data read from the data server 151.

Figure 11B:
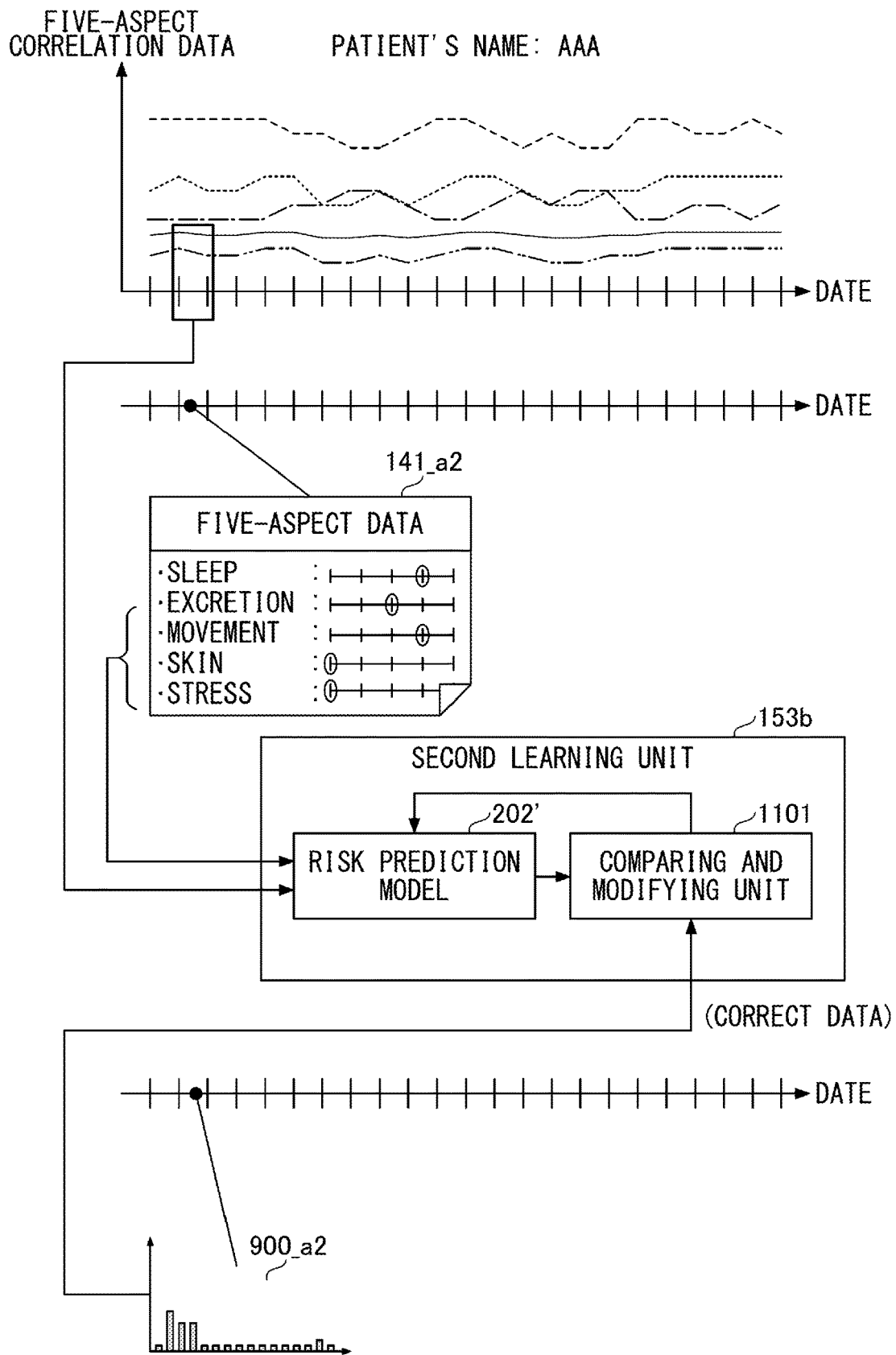
FIG. 11B is a second diagram illustrating an example of the functional configuration of the second learning unit.

FIG. 11B is a second diagram illustrating an example of the functional configuration of the second learning unit. A difference from FIG. 11B is that the second learning unit 153b reads the two-aspect correlation data among the five-aspect correlation data (in the example of FIG. 11B, the data correlating with the sleep and excretion conditions of the patient whose name is "AAA" on the second day). Additionally, the second learning unit 153b reads three-aspect data among the five-aspect data (in the example of FIG. 11B, the degree of the movement, the skin, and the stress of the patient whose name is "AAA" on the second day).

In FIG. 11B, the second learning unit 153b inputs the two-aspect correlation data on the second day and the three-aspect data on the second day into a risk prediction model 202'. Consequently, the second learning unit 153b executes the risk prediction model 202' and the risk prediction model 202' outputs the risk correlation data. Specifically, the risk prediction model 202' outputs the risk correlation data including items of "insomnia", "bedridden", "bedsores", "constipation", "pain", . . . , and the like.

The risk correlation data that is output from the risk prediction model 202' is input to the comparing and modifying unit 1101. The comparing and modifying unit 1101 compares the following data.
  the risk correlation data that is output from the risk prediction model 202'
  the risk correlation data calculated based on the risk occurrence information read from the data server 151 (the correct data)
The comparing and modifying unit 1101 modifies model parameters of the risk prediction model 202' in accordance with a comparison result.

As described, the second learning unit 153b performs machine learning on the risk prediction model 202' that determines a correspondence relationship between the following data.
  the two-aspect correlation data and the three-aspect data of the patient for the predetermined interval
  the risk correlation data of the one or more future risks that may occur with respect to the patient for the predetermined interval
Consequently, the second learning unit 153b generates a learned risk prediction model for inferring the risk correlation data.

In the example of FIG. 11B, the case in which the two-aspect correlation data and the three-aspect data are input has been described, but machine learning may be performed by inputting one-aspect correlation data and the four-aspect data. Alternatively, machine learning may be performed by inputting three-aspect correlation data and two-aspect data, or by inputting four-aspect correlation data and one-aspect data.

<Functional Configuration of the First Inference Unit>

Next, a functional configuration of the first inference unit 154a of the data analyzing device 152 will be described. Here, a case in which the inference is performed by using a different data set will be described.

(1) First Case

FIG. 12A is a first diagram illustrating an example of the functional configuration of the first inference unit. As illustrated in FIG. 12A, the first inference unit 154a includes the learned five-aspect calculation model 301.

The first inference unit 154a sequentially reads multiple actuator control patterns that are stored in the pattern storage unit 1201 in advance. Then, the first inference unit 154a determines environmental information obtained after the environment in the room where a new patient (a patient's name=XXX, and a subject) resides is changed by using each of the read actuator control patterns. The first inference unit 154a reads the current five-aspect correlation data of the new patient.

Then, the first inference unit 154a sequentially inputs the obtained changed environmental information to the learned five-aspect calculation model 301 together with the current five-aspect correlation data of the new patient (in the example of FIG. 12A, the 9th day) to execute the learned five-aspect calculation model 301. Consequently, the learned five-aspect calculation model 301 infers five-aspect correlation data 1210 corresponding to each environmental information.

Here, if the learned five-aspect calculation model 301 is generated by performing machine learning using only part of the temperature, the humidity, the atmospheric pressure, the illuminance, and the noise in the room, the first inference unit 154a inputs only the part to the learned five-aspect calculation model 301.

(2) Second Case

In the above-described first case, the case in which the first inference unit 154a includes the learned five-aspect calculation model 301 has been described. With respect to the above, in a second case, a case in which the first inference unit 154a includes a learned two-aspect calculation model 301' as an example of the first learned model will be described.

FIG. 12B is a second diagram illustrating an example of the functional configuration of the first inference unit. As illustrated in FIG. 12B, the first inference unit 154a includes the learned two-aspect calculation model 301'. The difference from FIG. 12A is that the first inference unit 154a reads the two-aspect correlation data of the new patient at the current time (in the example of FIG. 12A, the 9th day).

The first inference unit 154a executes the learned two-aspect calculation model 301' by sequentially inputting the obtained environmental information into the learned two-aspect calculation model 301', together with the current two-aspect correlation data of the new patient. Consequently, the learned two-aspect calculation model 301' infers two-aspect correlation data 1211 corresponding to each environmental information.

<Functional Configuration of the Second Inference Unit>

Figure 13:
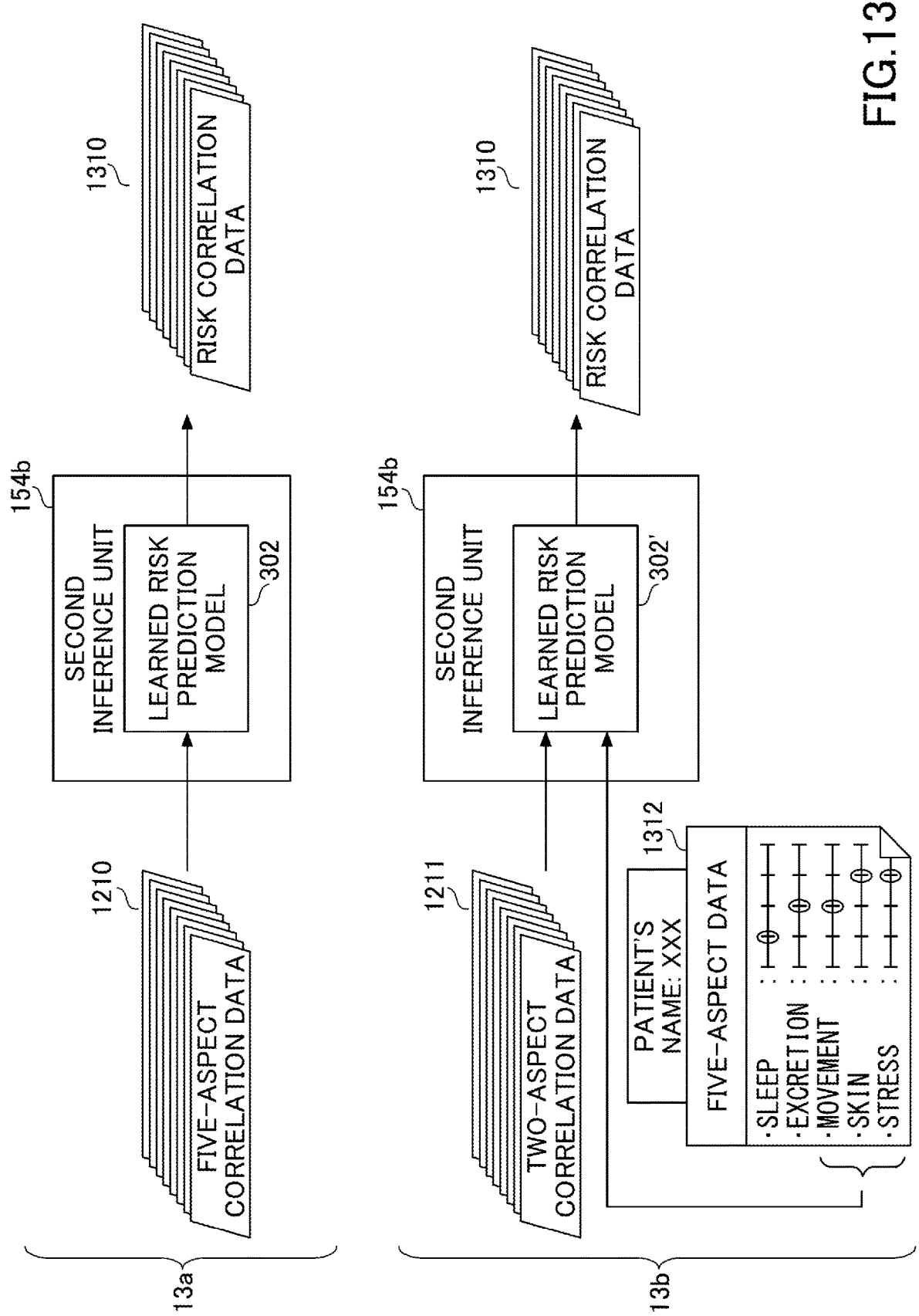
FIG. 13 is a diagram illustrating an example of a functional configuration of a second inference unit.

Next, a functional configuration of the second inference unit 154b of the data analyzing device 152 will be described. FIG. 13 is a diagram illustrating an example of the functional configuration of the second inference unit. In FIG. 13, the example of 13a of FIG. 13 indicates that the second inference unit 154b includes the learned risk prediction model 302.

The second inference unit 154b obtains the five-aspect correlation data that is sequentially output from the learned five-aspect calculation model 301 of the first inference unit 154a and inputs the data into the learned risk prediction model 302 to execute the learned risk prediction model 302. Consequently, the learned risk prediction model 302 infers risk correlation data 1310 corresponding to each of the five-aspect correlation data.

Specifically, the second inference unit 154b obtains data that correlates with the sleep, excretion, movement, skin, and stress conditions output from the learned five-aspect calculation model 301 and inputs the data into the learned risk prediction model 302 to infer the risk correlation data 1310.

With respect to the above, the example of 13b of FIG. 13 indicates a case in which the second inference unit 154b includes a learned risk prediction model 302', which is an example of a second learned model. The second inference unit 154b obtains data correlating with the sleep and excretion conditions output from the learned two-aspect calculation model 301' and inputs the data into the learned risk prediction model 302'. Additionally, the second inference unit 154b reads current five-aspect data 1312 of the new patient (in the example of FIG. 13, a patient whose name is "XXX") from the data server 151 and inputs the degrees of movement, skin, and stress into the learned risk prediction model 302. Consequently, the second inference unit 154b infers the risk correlation data 1310.

<Function Configuration of the Operating Condition Determining Unit>

Figure 14:
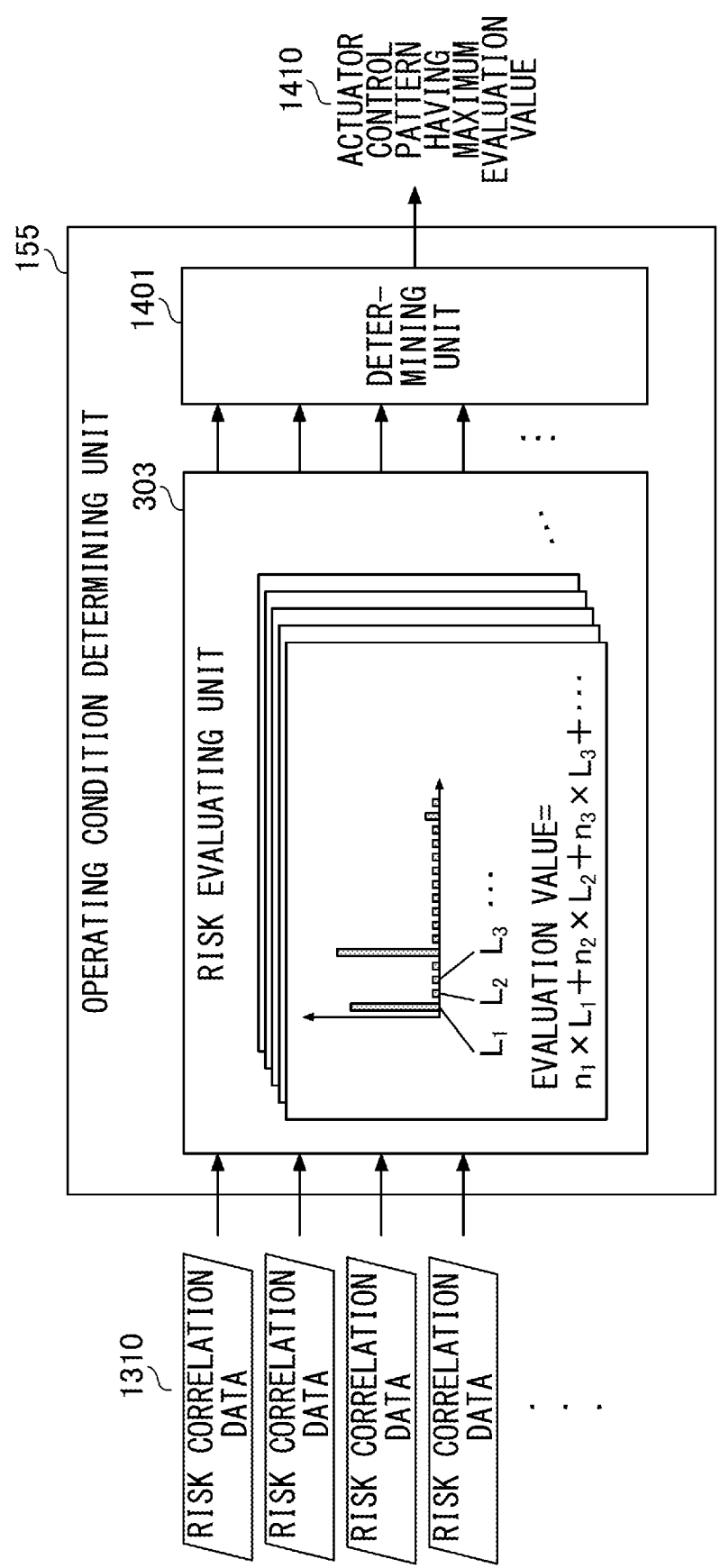
FIG. 14 is a diagram illustrating an example of a functional configuration of an operating condition determining unit.

Next, a functional configuration of the operating condition determining unit 155 of the data analyzing device 152 will be described. FIG. 14 is a diagram illustrating an example of the functional configuration of the operating condition determining unit. As illustrated in FIG. 14, the operating condition determining unit 155 includes the risk evaluating unit 303 and a determining unit 1401.

The operating condition determining unit 155 obtains the risk correlation data 1310 that is sequentially output from the learned risk prediction model 302 of the second inference unit 154b and inputs the risk correlation data 1310 to the risk evaluating unit 303.

The risk evaluating unit 303 calculates an evaluation value for each of the input risk correlation data 1310. The example of FIG. 14 indicates a case in which the evaluation value is calculated for risk correlation data that is first input among the risk correlation data 1310.

Specifically, the risk evaluating unit 303 calculates the evaluation value by weighting and adding values of respective items of the risk correlation data that is first input (insomnia=L1%, bedridden=L2%, bedsores=L3%, . . . ) based on the following equation.

$$\text{evaluation value} = n1 \times L1 + n2 \times L2 + n3 \times L3 + \ldots$$

The risk evaluating unit 303 calculates the evaluation value for each of the risk correlation data included in the risk correlation data 1310 and sequentially outputs results to the determining unit 1401.

The determining unit 1401 compares respective evaluation values that are output from the risk evaluating unit 303 and extracts the maximum evaluation value. Additionally, the determining unit 1401 determines an actuator control pattern 1410 corresponding to the extracted maximum evaluation value. That is, the determining unit 1401 determines the actuator control pattern 1410 having the best evaluation result.

The determining unit 1401 transmits the determined actuator control pattern 1410 to the actuator control system 110.

<Flow of a Data Analysis Process Performed by Data Analyzing Device>

Figure 15:
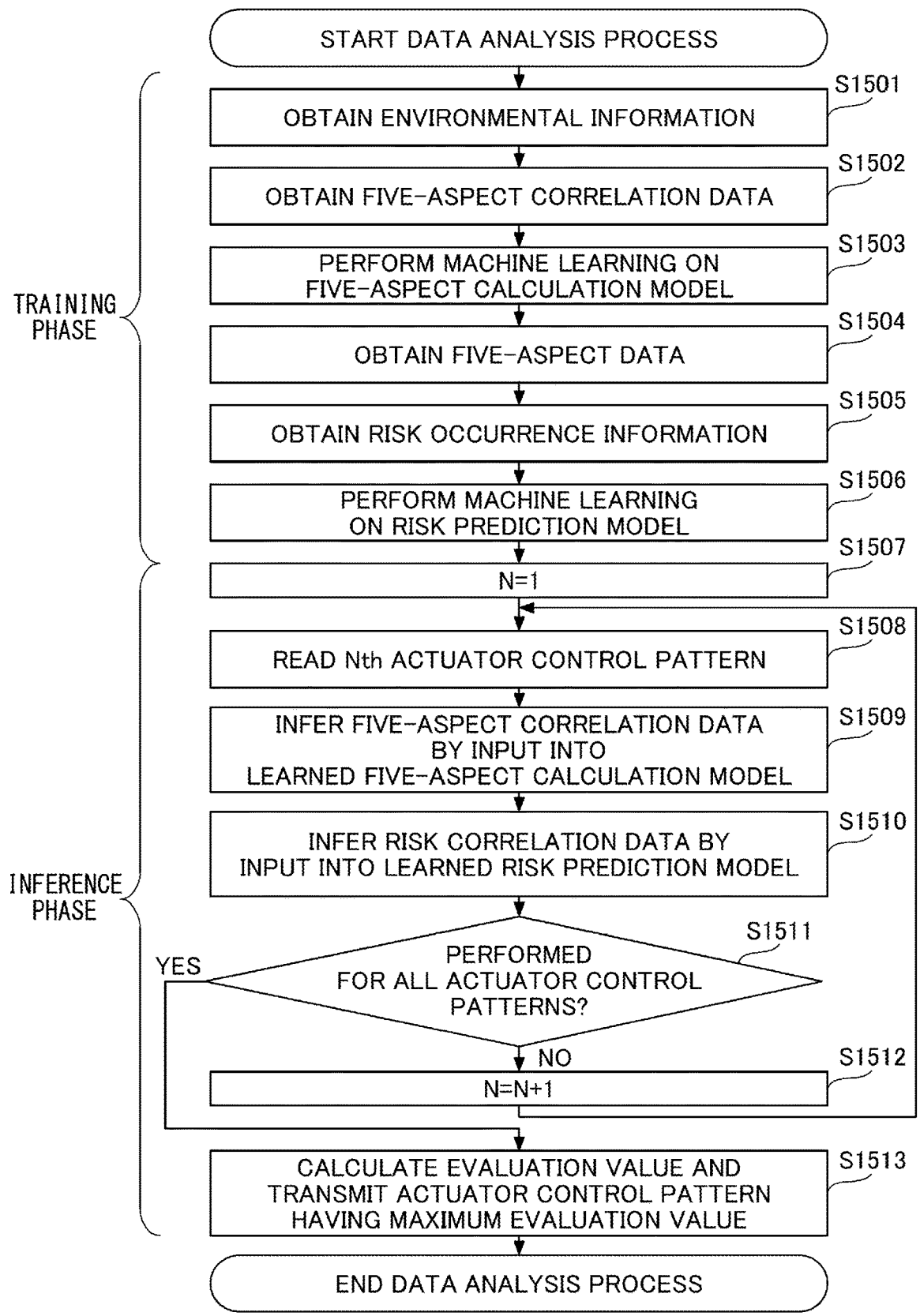
FIG. 15 is a flowchart illustrating a flow of a data analysis process performed by a data analyzing device.

Next, an entire flow of a data analysis process performed by the data analyzing device 152 will be described. FIG. 15 is a flowchart illustrating the flow of the data analysis process performed by the data analyzing device. Here, it is assumed that when the data analyzing device 152 performs the data analysis process, the patient attribute information for multiple patients, the environmental information, the five-aspect correlation data, the five-aspect data, and the risk occurrence information (the training data) are stored in the data server 151.

In step S1501, the first learning unit 153a obtains the environmental information from the data server 151.

In step S1502, the first learning unit 153a and the second learning unit 153b obtain the five-aspect correlation data from the data server 151.

In step S1503, the first learning unit 153a performs machine learning on the five-aspect calculation model 201 that determines a correspondence relationship between the environmental information and the five-aspect correlation data, and generates the learned five-aspect calculation model.

In step S1504, the second learning unit 153b obtains the five-aspect data from the data server 151.

In step S1505, the second learning unit 153b obtains the risk occurrence information from the data server 151 and calculates the risk correlation data.

In step S1506, the second learning unit 153b performs machine learning on the risk prediction model 202 that determines a correspondence relationship between the five-aspect correlation data (and the five-aspect data) and the risk correlation data, and generates the learned risk prediction model.

In step S1507, the first inference unit 154a inputs "1" to a counter N that counts the actuator control patterns.

In step S1508, the first inference unit 154a reads the Nth actuator control pattern among the multiple actuator control patterns stored in the pattern storage unit 1201 in advance. Additionally, the first inference unit 154a determines the environmental information obtained after the environment in the room where the new patient resides is changed by using the Nth actuator control pattern that is read.

In step S1509, the first inference unit 154a inputs the environmental information determined in step S1508 into the learned five-aspect calculation model and infers the five-aspect correlation data.

In step S1510, the second inference unit 154b inputs the inferred five-aspect correlation data and the current five-aspect data into the learned risk prediction model to infer the risk correlation data.

In step S1511, the first inference unit 154a determines whether the risk correlation data is inferred for all of the multiple actuator control patterns stored in the pattern storage unit 1201 in advance. In step S1511, if it is determined that there is an actuator control pattern by which the risk correlation data is not inferred (NO in step S1511), the process proceeds to step S1512.

In step S1512, the first inference unit 154a increments the counter N and the process returns to step S1508.

With respect to the above, if it is determined in step S1511 that the risk correlation data is inferred for all of the multiple actuator control patterns (YES in step S1511), the process proceeds to step S1513.

In step S1513, the operating condition determining unit 155 calculates the evaluation value for each of the inferred risk correlation data and determines an actuator control pattern corresponding to the maximum evaluation value. The operating condition determining unit 155 transmits the determined actuator control pattern to the actuator control system 110.

<Summary>

As can be seen from the above description, in the first embodiment, the following processes are performed.

perform learning by associating the environmental information indicating the environment of the patient with the five-aspect correlation data of the patient perform learning by associating the five-aspect correlation data of the patient with the risk correlation data of the one or more risks that may occur with respect to the patient in a future period of time infer the risk correlation data by inputting, into the learned risk prediction model, the five-aspect correlation data inferred by inputting, into the learned five-aspect calculation model, the environmental information obtained after the current environment of the new patient is changed, or infer the risk correlation data by inputting, into the learned risk prediction model, a combination of the inferred five-aspect correlation data and the current five-aspect data of the new patient evaluate the inferred risk correlation data to determine the operating condition of the actuator that controls the environment of the new patient As described, according to the first embodiment, before a problem event occurs in the patient, the risk of occurrence can be predicted and the environment of the patient can be optimized. That is, according to the first embodiment, a control system that optimally controls the environment of the patient can be provided. As a result, the occurrence of the problem event can be suppressed and the QOL of the patient can be improved.

Second Embodiment

In the above-described first embodiment, the case, in which the first learning unit 153a uses the environmental information for one day and the five-aspect correlation data for one day in performing the machine learning on the five-aspect calculation model 201, has been described. However, in performing the machine learning on the five-aspect calculation model 201, the environmental information for multiple days and the five-aspect correlation data for multiple days may be used.

Figure 16:
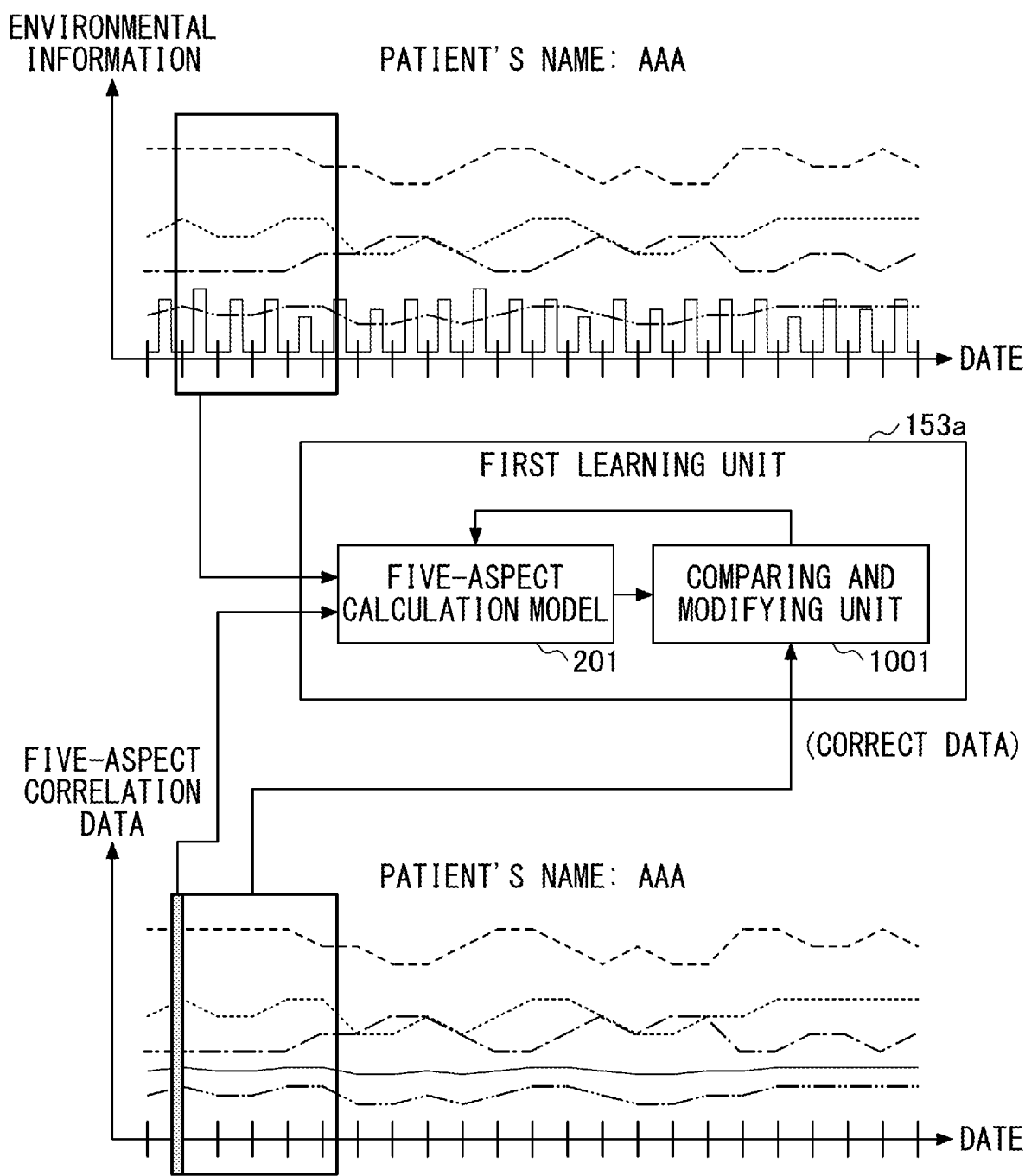
FIG. 16 is a first diagram illustrating another example of the functional configuration of the first learning unit.

FIG. 16 is a first diagram illustrating another example of the functional configuration of the first learning unit. The difference from FIG. 10 is the environmental information and the five-aspect correlation data read from the data server 151 by the first learning unit 153a.

Specifically, in FIG. 16, the first learning unit 153a reads the environmental information about the person whose name is AAA from the second day to the fifth day and the five-aspect correlation data from the second day to the fifth day from the data server 151.

The first learning unit 153a inputs the environmental information from the second day to the fifth day into the five-aspect calculation model 201 together with the five-aspect correlation data at the beginning of the second day. Consequently, the first learning unit 153a executes the five-aspect calculation model 201 and the five-aspect calculation model 201 outputs the five-aspect correlation data from the second day to the fifth day.

The five-aspect correlation data from the second day to the fifth day that is output from the five-aspect calculation model 201 is input to the comparing and modifying unit 1001. The comparing and modifying unit 1001 compares the following data.

the five-aspect correlation data from the second day to the fifth day that is output from the five-aspect calculation model 201 the five-aspect correlation data from the second day to the fifth day that is read from the data server 151 (correct data)

The comparing and modifying unit 1001 modifies model parameters of the five-aspect calculation model 201 based on a comparison result.

As described, the first learning unit 153a may perform machine learning on the five-aspect calculation model 201 that determines a correspondence relationship between the following data.

the environmental information indicating the environment of the patient for multiple days and five-aspect correlation data at the beginning of the multiple days the five-aspect correlation data of the patient for multiple days In this case, the second learning unit 153b performs machine learning on the risk prediction model 202 by inputting the five-aspect correlation data for multiple days. The first inference unit 154a infers the five-aspect correlation data for multiple days, and the second inference unit 154b infers the risk correlation data by inputting the five-aspect correlation data for multiple days.

As described, the accuracy of the inferred risk correlation data can be improved by using data for multiple days.

Third Embodiment

In the above-described first and second embodiments, the case, in which the first learning unit 153a inputs the environmental information when performing the machine learning on the five-aspect calculation model 201, has been described. However, in performing the machine learning on the five-aspect calculation model 201, patient attribute information may be further input.

Figure 17:
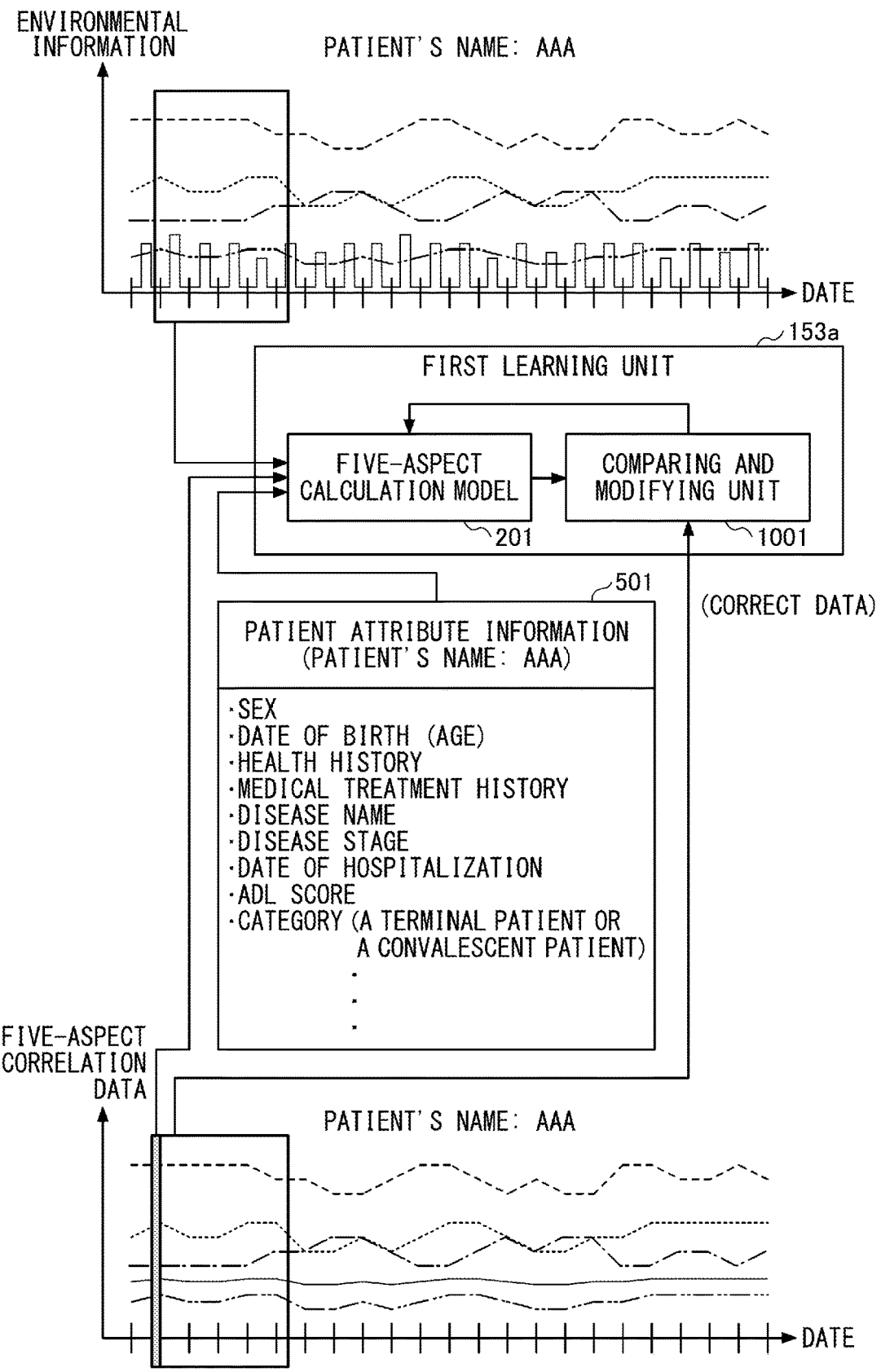
FIG. 17 is a second diagram illustrating another example of the functional configuration of the first learning unit.

FIG. 17 is a second view illustrating another example of the functional configuration of the first learning unit. The difference from FIG. 10 is that the first learning unit 153a reads the patient attribute information 501 from the data server 151.

Specifically, in FIG. 17, the first learning unit 153a reads the environmental information about the patient whose name is "AAA" on the second day from the data server 151. Additionally, the first learning unit 153a reads the patient attribute information 501 about the patient whose name is "AAA". Furthermore, the first learning unit 153a reads the five-aspect correlation data of the patient whose name is "AAA" at the beginning of the second day and the five-aspect correlation data on the second day.

The first learning unit 153a inputs, into the five-aspect calculation model 201, the environmental information about the patient whose name is "AAA" on the second day, the patient attribute information 501 about the patient whose name is "AAA", and the five-aspect correlation data of the patient whose name is "AAA" at the beginning of the second day. Consequently, the first learning unit 153a executes the five-aspect calculation model 201 and the five-aspect calculation model 201 outputs the five-aspect correlation data.

The five-aspect correlation data that is output from the five-aspect calculation model 201 is input to the comparing and modifying unit 1001. The comparing and modifying unit 1001 compares the following data.

the five-aspect correlation data that is output from the five-aspect calculation model 201 the five-aspect correlation data read from the data server 151 (the correct data) The comparing and modifying unit 1001 modifies model parameters of the five-aspect calculation model 201 based on a comparison result.

As described, the first learning unit 153a performs machine learning on the five-aspect calculation model 201 that determines a correspondence relationship between the following data.
- a combination of the environmental information indicating the environment of the patient for the predetermined interval, the five-aspect correlation data at the beginning of the predetermined interval, and the patient attribute information
- the five-aspect correlation data of the patient for the predetermined interval Here, the patient attribute information is input to the first learning unit 153a, but the patient attribute information may be input to the second learning unit 153b. In this case, the second learning unit 153b performs machine learning on the risk prediction model 202 that determines a correspondence relationship between the following data.
- a combination of the five-aspect correlation data of the patient for the predetermined interval and the patient attributes information
- the risk correlation data of the one or more risks that may occur with respect to the patient in a future period of time If the patient attribute information is input to the first learning unit 153a, the patient attribute information is also input to the first inference unit 154a, and if the patient attribute information is input to the second learning unit 153b, the patient attribute information is also input to the second inference unit 154b.

As described, by using the patient attribute information, the risk correlation data can be inferred according to the value of each item included in the patient attribute information, such as sex, age, medical history, . . . , thereby improving the accuracy of the risk correlation data.

Fourth Embodiment

Figure 18:
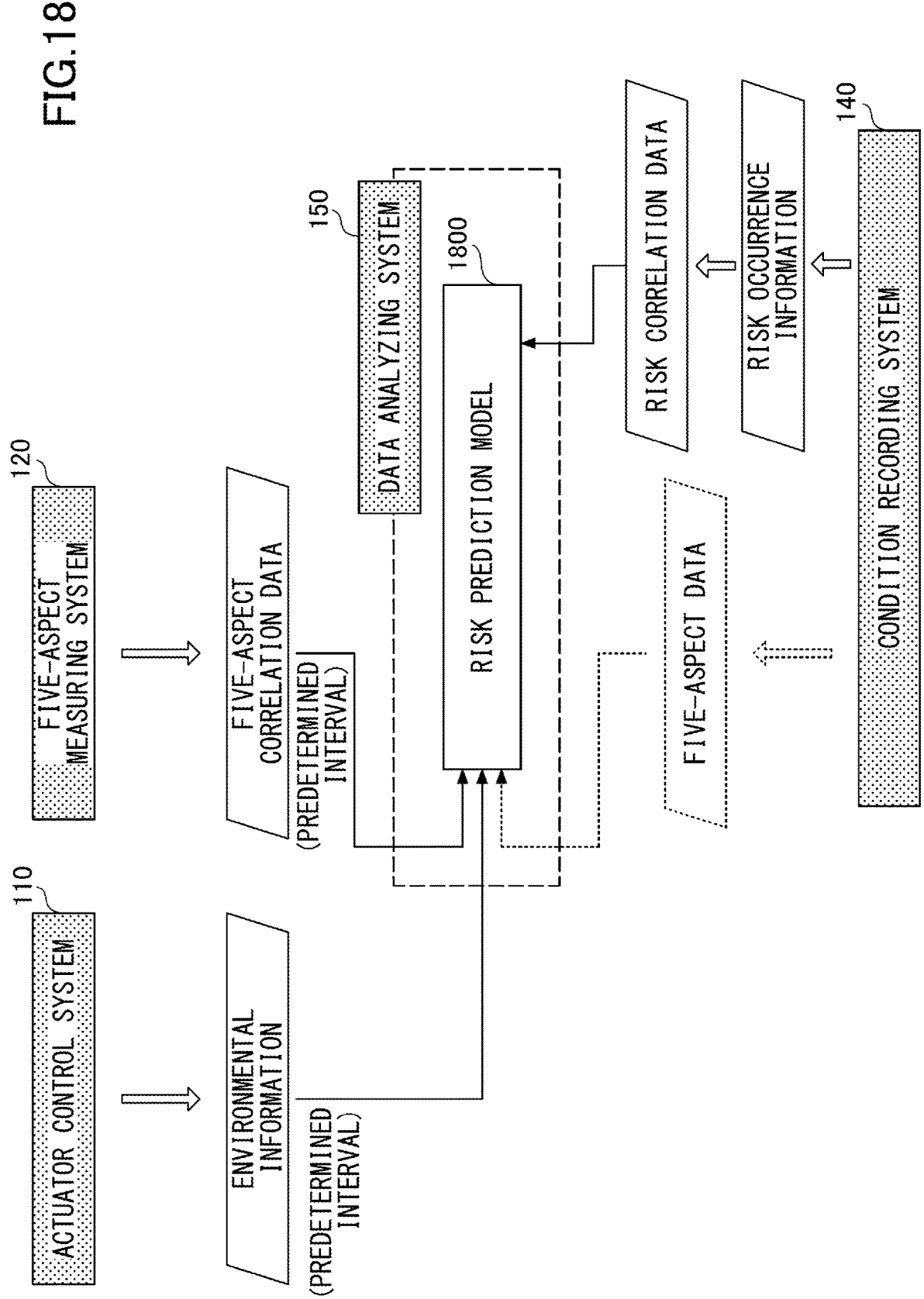
FIG. 18 is a diagram for explaining an outline of a process of an environment control system (a training phase) according to a fourth embodiment.
Figure 19:
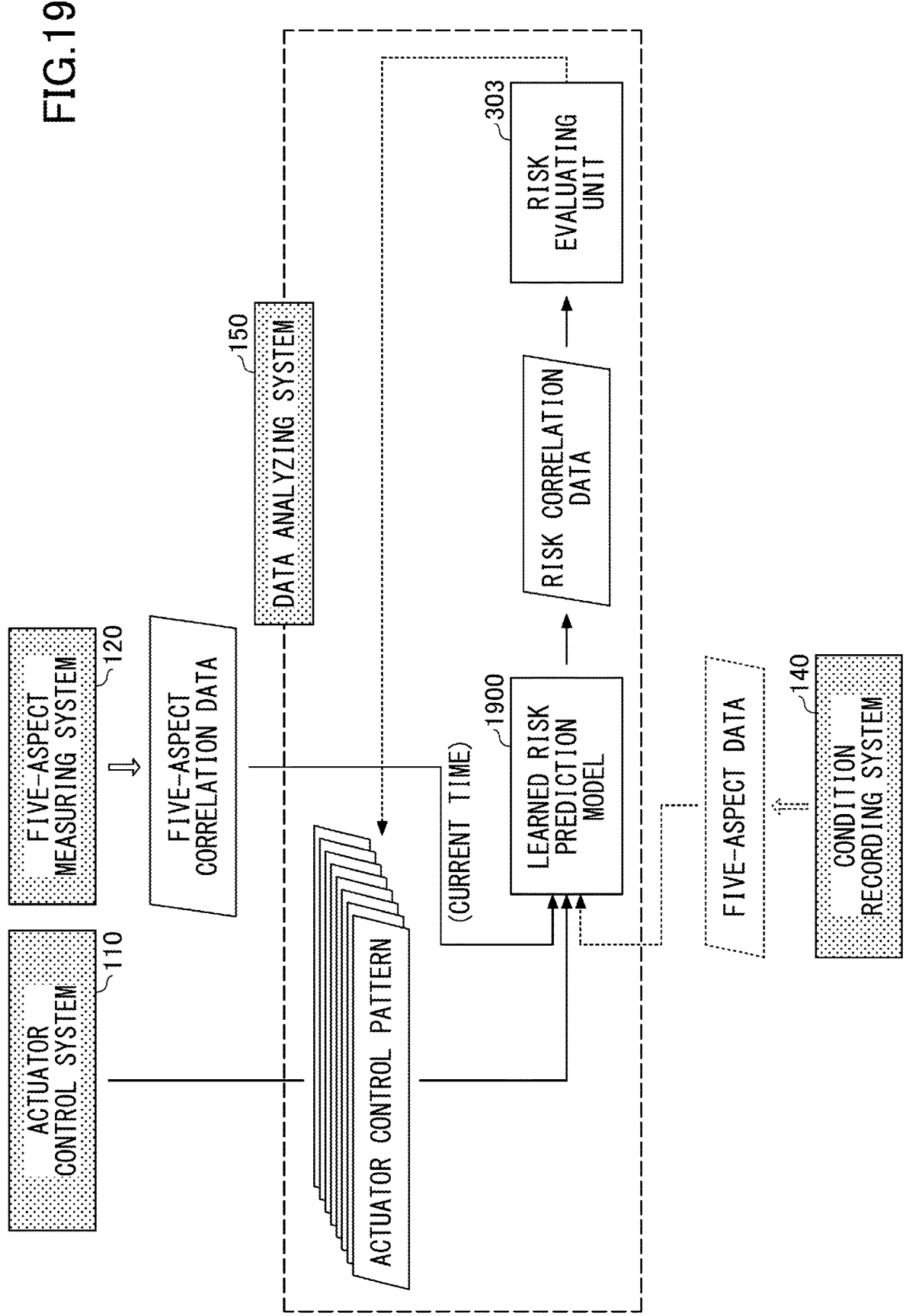
FIG. 19 is a diagram for explaining an outline of a process of the environment control system (an inference phase) according to the fourth embodiment.

In the above-described first to third embodiments, the case, in which the data analyzing system 150 includes the five-aspect calculation model 201 and the risk prediction model 202, has been described. In contrast, in a fourth embodiment, a case, in which the data analyzing system 150 includes only the risk prediction model, will be described.
(1) Outline of a Process of the Environment Control System in the Training Phase FIG. 18 is a diagram for explaining an outline of a process of the environment control system (in the training phase) according to the fourth embodiment. As illustrated in FIG. 18, in the data analyzing system 150 according to the fourth embodiment, a risk prediction model 1800 generates a learned risk prediction model by performing machine learning by inputting the environmental information for the predetermined interval transmitted from the actuator control system 110 and m-aspect correlation data transmitted from the five-aspect measuring system 120 (and (5-m)-aspect data transmitted from the condition recording system 140), and by using, as the correct data, the risk correlation data calculated based on the risk occurrence information transmitted from the condition recording system 140.
(2) Outline of a Process of the Environment Control System in the Inference Phase FIG. 19 is a diagram for explaining an outline of a process of the environment control system (in the inference phase) according to the fourth embodiment. As illustrated in FIG. 19, in the data analyzing system 150 according to the fourth embodiment, a learned risk prediction model 1900, which is an example of a third learned model, infers respective risk correlation data by inputting the following data.
- the multiple environmental information obtained after the current environment of the new patient is changed based on multiple different actuator control patterns
- the current m-aspect correlation data of the new patient that is transmitted from the five-aspect measuring system 120 (and the current (5-m)-aspect data of the new patient that is transmitted from the condition recording system 140)

In the data analyzing system 150, the risk evaluating unit 303 evaluates the risk correlation data that is output from the learned risk prediction model 1900. The risk evaluating unit 303 evaluates the risk correlation data output from the learned risk prediction model 1900 every time one actuator control pattern is input to the learned risk prediction model 1900.

When the risk evaluating unit 303 completes the evaluation of all the risk correlation data, the actuator control pattern having the best evaluation result is determined. Consequently, the determined actuator control pattern is transmitted to the actuator control system 110 as the optimum actuator control pattern that controls the current environment of the new patient.

As described, in the fourth embodiment, the data analyzing system generates one learned model (i.e., the learned risk prediction model) and infers the risk correlation data by using the one learned model.

Also in this case, as in the first embodiment, before a problem event occurs in the patient, the risk of the occurrence can be predicted and the environment of the patient can be optimized. That is, according to the fourth embodiment, the environment control system that optimally controls the environment of the patient can be provided. As a result, the occurrence of the problem event can be suppressed and the QOL of the patient can be improved.

Other Embodiments

In the above-described first embodiment, the case, in which the data analyzing device 152 includes the first learning unit 153a, the second learning unit 153b, the first inference unit 154a, the second inference unit 154b, and the operating condition determining unit 155 in the data analyzing system 150, has been described. However, each unit included in the data analyzing device 152 may be configured in a separate device within the data analyzing system 150. Alternatively, part of the units of the data analyzing device 152 (e.g., the operating condition determining unit 155) may be implemented, for example, in the actuator control system 110.

In the above-described first to third embodiments, the case, in which in executing the five-aspect calculation model 201 and the two-aspect calculation model 201', the five-aspect correlation data and the two-aspect correlation data at the beginning of the predetermined interval are input, have been described. However, the five-aspect correlation data and the two-aspect correlation data at the beginning of the predetermined interval may not be required to be input (i.e., learning may be performed by associating the environmental information for the predetermined interval with the five-aspect correlation data for the predetermined interval). In this case, the learned five-aspect calculation model 301 and the learned two-aspect calculation model 301' are generated as more general models independent of a condition of an individual patient.

In the above-described first to third embodiments, the case in which in executing the learned risk prediction model 302', the second inference unit 154b, for example, inputs the following data, has been described.

the two-aspect correlation data 1211 that is output from the learned two-aspect calculation model 301'
the degree of the movement, the skin, and the stress of the current five-aspect data 1312

However, a combination of data input into the learned risk prediction model 302' is not limited to this. For example, part of the current five-aspect data 1312 may be replaced with corresponding data of the current five-aspect correlation data.

Specifically, in executing the learned risk prediction model 302', the second inference unit 154b may, for example, input the following data.

the two-aspect correlation data 1211 that is output from the learned two-aspect calculation model 301'
the degree of the movement and the skin among the current five-aspect data 1312
data correlating with the stress among the current five-aspect correlation data That is, the "data related to the condition of the patient" described in the above-described first to third embodiments includes either or both of the current five-aspect data and the current five-aspect correlation data.

In the above-described first embodiment, the models (the five-aspect calculation model, the two-aspect calculation model, model, and the risk prediction model) used to perform machine learning are specifically described in detail, but any type of model may be applied to a model used to perform machine learning. Specifically, any type of model, such as a neural network (NN) model, a random forest model, and a support vector machine (SVM) model may be applied.

In the above-described first embodiment, a method of changing model parameters when changing the model parameters based on comparison results obtained by the comparing and modifying unit is not described in detail. However, the method of changing model parameters that is performed by the comparing and modifying unit may be selected according to the type of model.

Although the embodiments have been described above, it will be understood that various modifications of forms and the detail can be made without departing from the spirit and scope of the claims.

This application is based upon and claims priority to Japanese Patent Application No. 2019-049194, filed Mar. 15, 2019, and Japanese Patent Application No. 2020-003216, filed Jan. 10, 2020, the entire contents of which are incorporated herein by reference.

DESCRIPTION OF THE REFERENCE NUMERALS

100: environment control system
110: actuator control system
115: actuator control device
116: collector
117: controller
120: five-aspect measuring system
140: condition recording system
141: five-aspect data
142: risk occurrence information
150: data analyzing system
151: data server
152: data analyzing device
153a: first learning unit
153b: second learning unit
154a: first inference unit
154b: second inference unit
155: operating condition determining unit
201: five-aspect calculation model
202: risk prediction model
301: learned five-aspect calculation model
302: learned risk prediction model
303: risk evaluating unit
501-503: patient attribute information
900_a1, etc.: risk correlation data
1401: determining unit
1800: risk prediction model
1900: learned risk prediction model

The invention claimed is:
1. An environment control system, comprising:
an actuator configured to control an environment;
a processor configured to determine an operating condition of the actuator and configured to control the actuator based on the operating condition;
a memory storing a first learned model and a second learned model, the processor being coupled to the memory,
wherein the first learned model has been trained by associating environmental information indicating an environment of a subject with condition correlation data correlating with at least one of sleep, excretion, movement, skin, and stress conditions of the subject,
wherein the second learned model has been trained by associating the condition correlation data with risk correlation data correlating with a magnitude of one or more risks that may occur with respect to the subject in a future period of time,
wherein the processor infers risk correlation data correlating with the magnitude of the one or more risks by inputting, into the second learned model, data that is output from the first learned model upon inputting environmental information about a target subject into the first learned model, or a combination of the data that is output from the first learned model upon inputting the environmental information about the target subject into the first learned model and data related to a condition of the target subject,
wherein the processor evaluates the inferred risk correlation data to determine the operating condition of the actuator,
wherein the processor inputs the environmental information indicating the environment of the target subject into the first learned model to obtain the output data that is output from the first learned model, and inputs the obtained output data into the second learned model to infer the risk correlation data,
wherein the first learned model has been trained, for each of a plurality of subjects, by inputting the environmental information indicating the environment of the subject for a predetermined period of time and the condition correlation data at a beginning of the predetermined period of time into the first learned model and comparing an output of the first learned model with the condition correlation data for the predetermined period of time, parameters of the first learned model being modified in accordance with a result of the comparing of the output of the first learned model with the condition correlation data for the predetermined period of time, wherein the second learned model has been trained, for each of the plurality of subjects, by inputting the condition correlation data for the predetermined period of time into the second learned model and comparing an output of the second learned model with the risk correlation data, parameters of the second learned model being modified in accordance with a result of the comparing of the output of the second learned model with the risk correlation data, wherein the processor inputs, into the first learned model, the environmental information about the target subject generated based on each of a plurality of actuator control patterns, and infers a plurality of risk correlation data, and wherein the processor evaluates the plurality of risk correlation data and identifies an optimum actuator control pattern among the plurality of actuator control patterns to determine the operating condition of the actuator.

2. The environment control system as claimed in claim 1, wherein the second learned model is trained by using biological information about the subject as the condition correlation data.

3. The environment control system as claimed in claim 2, wherein the biological information includes at least one of an amount of movement of the subject, a number of times scratching of the subject, a fluctuation of a heart rate of the subject, a depth of sleep of the subject, an estimated amount of urine of the subject, and a number of excretions of the subject.

4. The environment control system as claimed in claim 1, wherein the first learned model is trained by using the environmental information about the subject and the condition correlation data as a training data set.

5. The environment control system as claimed in claim 4, wherein the first learned model is trained based on the condition correlation data of the subject and a combination of the environmental information about the subject and attribute information indicating an attribute of the subject.

6. The environment control system as claimed in claim 1, wherein the second learned model has been trained by using the condition correlation data and the risk correlation data as a training data set.

7. The environment control system as claimed in claim 1, wherein the processor uses a nursing record as the data related to the condition of the subject.

8. The environment control system as claimed in claim 1, wherein the processor evaluates the inferred risk correlation data by weighting and adding the inferred risk correlation data.

9. The environment control system as claimed in claim 1, wherein the environmental information includes at least one of a temperature, a humidity, an atmospheric pressure, an illuminance, and a noise.

10. The environment control system as claimed in claim 1, wherein the actuator includes an air conditioning device that controls the environment of the subject.

11. An environment control system, comprising:
an actuator configured to control an environment;
a processor configured to determine an operating condition of the actuator and configured to control the actuator based on the operating condition;
a memory storing a third learned model, the processor being coupled to the memory,
wherein the third learned model has been trained by associating condition correlation data correlating with at least one of sleep, excretion, movement, skin, and stress conditions of a subject, environmental information indicating an environment of the subject, with risk correlation data correlating with a magnitude of one or more risks that may occur with respect to the subject in a future period of time,
wherein the processor infers risk correlation data correlating with the magnitude of the one or more risks by inputting data correlating with at least one of sleep, excretion, movement, skin, and stress conditions of a target subject and environmental information about the target subject into the third learned model,
wherein the processor evaluates the inferred risk correlation data to determine the operating condition of the actuator,
wherein the third learned model has been trained, for each of a plurality of subjects, by inputting the condition correlation data at a beginning of a predetermined period of time and the environmental information indicating the environment of the subject for the predetermined period of time into the third learned model, and comparing an output of the third learned model with the risk correlation data, parameters of the third learned model being modified in accordance with a result of the comparing of the output of the third learned model with the risk correlation data,
wherein the processor inputs, into the third learned model, the environmental information about the target subject generated based on each of a plurality of actuator control patterns, and infers a plurality of risk correlation data, and
wherein the processor evaluates the plurality of risk correlation data and identifies an optimum actuator control pattern among the plurality of actuator control patterns to determine the operating condition of the actuator.

* * * * *